United States Patent
Novelli et al.

(10) Patent No.: US 10,842,430 B1
(45) Date of Patent: Nov. 24, 2020

(54) EYE FATIGUE DETECTION USING VISUAL IMAGING

(71) Applicant: Logitech Europe S.A., Lausanne (CH)

(72) Inventors: Ludovico Novelli, Geneva (CH); Olivier Theytaz, Savigny (CH)

(73) Assignee: Logitech Europe S.A., Lausanne (CH)

( * ) Notice: Subject to any disclaimer, the term of this patent is extended or adjusted under 35 U.S.C. 154(b) by 0 days.

(21) Appl. No.: 16/569,315

(22) Filed: Sep. 12, 2019

(51) Int. Cl.
*A61B 5/00* (2006.01)
*A61B 5/16* (2006.01)
*G02B 27/00* (2006.01)
*G06F 3/01* (2006.01)

(52) U.S. Cl.
CPC .......... *A61B 5/163* (2017.08); *G02B 27/0093* (2013.01); *G06F 3/013* (2013.01); *G06T 2207/30041* (2013.01)

(58) Field of Classification Search
CPC ..... A61B 5/163; G02B 27/0093; G06F 3/013; G06T 2207/30041
See application file for complete search history.

(56) References Cited

U.S. PATENT DOCUMENTS

| | | | |
|---|---|---|---|
| 7,572,008 B2 | 8/2009 | Elvesjo et al. | |
| 8,120,577 B2 | 2/2012 | Bouvin et al. | |
| 8,610,768 B2 | 12/2013 | Holmberg et al. | |
| 9,213,404 B2 | 12/2015 | Elvesjo et al. | |
| 10,203,758 B2 | 2/2019 | Bjorklund et al. | |
| 2011/0013007 A1* | 1/2011 | Holmberg | G06K 9/00604 348/78 |
| 2013/0050070 A1* | 2/2013 | Lewis | G06K 9/00604 345/156 |
| 2015/0145777 A1* | 5/2015 | He | G06F 3/0325 345/158 |
| 2016/0004303 A1* | 1/2016 | Arar | G06F 3/013 345/156 |
| 2018/0032136 A1* | 2/2018 | Kim | G06F 3/013 |
| 2020/0242800 A1* | 7/2020 | Chen | G06T 7/74 |

OTHER PUBLICATIONS

Wikipedia, "MS Kinect for Xbox 360" Retrieved on Jan. 8, 2020. Retrieved from Internet: <https://en.wikipedia.org/wiki/Kinect>, 25 pages.

Wikipedia, "MS Kinect for Windows" Retrieved on Jan. 8, 2020. Retrieved from Internet: <https://en.wikipedia.org/wiki/Kinect>, 25 pages.

(Continued)

*Primary Examiner* — Khai M Nguyen
(74) *Attorney, Agent, or Firm* — Kilpatrick Townsend & Stockton LLP

(57) ABSTRACT

Eye fatigue from looking too long at a computer monitor can not only cause physical symptoms, it can also reduce productivity. Eye tracking is used to determine potential eye fatigue. After potential eye fatigue is determined, an eye fatigue mitigation action is triggered. Eye fatigue mitigation action can including providing a notification, blurring a screen, and blanking a screen. Eye tracking can also be used to verify that a user has taken an eye fatigue mitigation action, such as diverted looking from a screen for a sufficient amount of time. By implementing eye fatigue mitigation actions, symptoms can be reduced and/or productivity increased.

20 Claims, 11 Drawing Sheets

(56) References Cited

OTHER PUBLICATIONS

Microsoft, "MS Azure Kinect DK" Retrieved on Jan. 8, 2020. Retrieved from Internet: <https://www.microsoft.com/en-us/p/azure-kinect-dk/8pp5vxmd9nhq?activetab=pivot%3aoverviewtab>, 5 pages.
Tobii, "Tobii Eye Tracker 4C" Retrieved on Jan. 8, 2020. Retrieved from Internet: <https://gaming.tobii.com/tobii-eye-tracker-4c/>, 7 pages.
Tobii, "Tobii Pro X3-120" Retrieved on Jan. 8, 2020. Retrieved from Internet: <https://www.tobiipro.com/product-listing/tobii-pro-x3-120/>, 11 pages.
Tobii, "Tobii Aware" Retrieved on Jan. 8, 2020. Retrieved from Internet: <https://help.tobii.com/hc/en-us/articles/213597409-Tobii-Aware-Features>, 6 pages.
Tadas Baltrusaitis et al., "OpenFace 2.0: Facial Behavior Analysis Toolkit" 2018 13th IEEE International Conference on Automatic Face Gesture Recognition (FG 2018), pp. 59-66, 2018, 8 pages.
Lech Swirski et al., "Robust real-time pupil tracking in highly off-axis images" Eye Tracking Research and Applications Symposium (ETRA), pp. 173-176, Mar. 2012, 4 pages.
Kevin W. Bowyer et al., "Cosmetic contact lenses and iris recognition spoofing" Computer- Published by the IEEE Computer Society, vol. 47: pp. 96-98, 2014, 3 Pages.
Erroll Wood et al., "Learning an appearance-based gaze estimator from one million synthesised images" ETRA '16—Published Mar. 14-17, 2016 Charleston, SC, USA, 8 pages.
Chao Gou et al., "A joint cascaded framework for simultaneous eye detection and eye state estimation." *Pattern Recognition*, vol. 67, pp. 23-31, Published by Elsevier Ltd., Jul. 2017, 9 pages.
Bin Li et al., "Real time eye detector with cascaded convolutional neural networks" *Applied Computational Intelligence and Soft Computing*, vol. 2018, pp. 1-8, Published by Hindawi, Apr. 2018, 9 pages.
Seonwook Park et al., "Learning to find eye region landmarks for remote gaze estimation in unconstrained settings." In *ACM Symposium on Eye Tracking Research and Applications (ETRA)*, ETRA '18 Published by Association for Computing Machinery, New York, NY, USA, Jun. 14-17, 2018, 10 pages.
Chao Gou et al., "Cascade learning from adversarial synthetic images for accurate pupil detection." *Pattern Recognition*, vol. 88, pp. 584-594, Published by Elsevier Ltd., Apr. 2019, 11 pages.
Fabian Timm et al., "Accurate eye centre localisation by means of gradients." pp. 125-130, Jan. 2011, 6 pages.
Anjith George et al., "A fast and accurate algorithm for eye localization for gaze tracking in low resolution images." *IET Computer Vision*, Published by IET Digital Library, vol. 10, Mar. 2016, 12 pages.

Tibor Moraveik, "An approach to iris and pupil detection in eye image" XII International PhD Workshop, OWD 2010, Oct. 23-26, 2010, 4 pages.
Amir-Homayoun Javadi et al., "Set: a pupil detection method using sinusoidal approximation." *Frontiers in Neuroengineering*, vol. 8, Article 4, Published Apr. 9, 2015, 10 pages.
Hugo Proena et al, "Introduction to the special issue on the segmentation of visible wavelength iris images captured at-a-distance and on-the-move." *Image Vision Comput.*, vol. 28, pp. 213-214, 2010, 2 pages.
Andrew W. Fitzgibbon et al., "A buyer's guide to conic fitting." In *BMVC*, 1995, 10 pages.
Pedro De Almeida, "A knowledge-based approach to the iris segmentation problem". *Image and Vision Computing*, 28(2):238-245, 2010. Segmentation of Visible Wavelength Iris Images Captured At-a-distance and On-the-move.
P. Jonathon Phillips et al., "The feret database and evaluation procedure for face-recognition algorithms." *Image Vision Computing*, Published by Elseview , vol. 16, pp. 295-306, 1998, 12 pages.
Michael J. Lyons et al., "Coding facial expressions with gabor wavelets." *Proceedings Third IEEE International Conference on Automatic Face and Gesture Recognition*, pp. 200-205, Apr. 14-16, 1998, 6 pages.
Gary B. Huang et al. "Labeled faces in the wild: A database for studying face recognition in unconstrained environments." Technical Report 07-49, University of Massachusetts, Amherst, Oct. 2007, 11 pages.
Victoria Ponz et al., Dataset for the evaluation of eye detector for gaze estimation. In *UbiComp*, PETMEI, Pittsburg, PA, Sep. 8, 2012, 23 pages.
Oliver Jesorsky et al., "Robust face detection using the hausdorff distance". Third International Conference on Audio- and Video-based Biometric Person Authentication, Springer, Lecture Notes in Computer Science, LNCS-2091, pp. 90-95, Halmstad, Sweden, Jun. 6-8, 2001, 6 pages.
Face++ Cognitive Services. Retrieved on Jan. 10, 2020. Retrieved from Internet: <https://www.faceplusplus.com/dense-facial-landmarks/.> , 3 pages.
Visage Technologies AB. Retrieved on Jan. 10, 2020. Retrieved from Internet: <http://visagetechnologies.com/.>, 7 pages.
Tieniu Tan et al, "Efficient and robust segmentation of noisy iris images for non-cooperative iris recognition." *Image and Vision Computing*, 28(2):223-230, 2010. Segmentation of Visible Wavelength Iris Images Captured At-a-distance and On-the-move.
Xucong Zhang et al. "Appearance-based gaze estimation in the wild." In *Proc. of the IEEE Conference on Computer Vision and Pattern Recognition (CVPR)*, Jun. 2015.

\* cited by examiner

EYE FATIGUE DETECTION USING VISUAL IMAGING

CROSS-REFERENCES TO RELATED APPLICATIONS

The following two U.S. patent applications (including this one) are being filed concurrently, and the entire disclosure of the other applications are incorporated by reference into this application for all purposes:

Application Ser. No. 16/569,315, filed Sep. 12, 2019, entitled "Eye Fatigue Detection Using Visual Imaging"; and Application Ser. No. 16/569,320, filed Sep. 12, 2019, entitled "Techniques for Eye Fatigue Mitigation".

BACKGROUND OF THE INVENTION

This application relates to eye strain, and more particularly, and without limitation, to mitigating eye strain. Eye strain has been known to be caused by viewing computer monitors. Symptoms related to eye strain can include fatigue, eye pain, pain around the eyes, blurred vision, headache, and double vision. Computer use can strain the eyes more than reading printed material because screens can contain higher amounts of glare, people often position themselves too closely to computer screens, and people tend to blink less when viewing computer screens. Eye strain can make people feel tired and reduce their ability to concentrate, which can result in decreased productivity. Accordingly, there exists a need to mitigate eye strain.

BRIEF SUMMARY

In some embodiments, an system for determining eye fatigue can include a computing device having a screen, a camera having an image sensor, one or more processors, and one or more memory devices containing instructions. The image sensor can be configured to detect visible light. The camera can be attached to, or be part of, the computing device. The instructions can cause the one or more processors to track, using a plurality of visible light images detected by the camera, a position of a pupil of a user in relation to the camera, where the plurality of visible light images are acquired over a time period; determine a gaze direction of the user over the time period, where gaze direction is based on the tracked position of the pupil; calculate a length of time during the time period that the gaze direction of the user is directed to a specified region corresponding to the screen of the computing device; determine that the length of time the gaze direction of the user is directed to the screen exceeds a threshold value within the time period considered to be unhealthy; determine, based on the length of time exceeding the threshold value, that an eye fatigue mitigation action is warranted to mitigate eye fatigue of the user; and/or trigger an eye fatigue mitigation action, based on determining that the eye fatigue mitigation action is warranted, where the eye fatigue mitigation action blurs the screen so that the user will be encouraged to look away from the screen. The plurality of visible light images can be a first plurality of visible light images; the time period can be a first time period; the length of time can be a first length of time; the threshold value can be a first threshold value; and/or the instructions can further configure the one or more processors to receive a second plurality of visible light images acquired by the camera, where: the second plurality of visible light images can be acquired over a second time period, and the second time period can be after the first time period; calculate, using the second plurality of visible light images, that the gaze direction of the user not at the screen for a second length of time within the second time period; determine that the second length of time exceeds a second threshold value within the second time period; and/or stop the eye fatigue mitigation action based on determining that the second length of time exceeds the second threshold value, such that the user has looked away from the screen to mitigate eye fatigue, where stopping the eye fatigue mitigation action reverses blurring the screen.

In some embodiments, an apparatus can include a camera, one or more processors, and one or more non-transitory memory devices containing instructions. The camera can have an image sensor, where the image sensor is configured to detect visible light. The instructions can cause the one or more processors to track, using a plurality of visible light images detected by the camera, a position of a pupil of a user in relation to the camera, where the plurality of visible light images are acquired over a time period; determine a gaze direction of the user over the time period, where gaze direction is based on the tracked position of the pupil; calculate a length of time during the time period that the gaze direction of the user is directed to a specified region corresponding to a display; determine that the length of time the gaze direction of the user is directed to the specified region exceeds a threshold value within the time period; and/or determine, based on the length of time exceeding the threshold value, that an eye fatigue mitigation action is warranted to mitigate eye fatigue of the user. In some embodiments, the instructions can cause the one or more processors to: determine a first blink rate of the user for a first duration based on a first portion of the plurality of visible light images; determine a second blink rate of the user for a second duration based on a second portion of the plurality of visible light images; determine that a blink rate of the user has slowed based on the second blink rate being slower than the first blink rate, where the determining that the eye fatigue mitigation action is warranted is based on the determining that the blink rate of the user has slowed; track a blink rate of the user based on the plurality of visible light images; determine that the blink rate has slowed below a threshold value based on the tracking the blink rate of the user, where the determining that the eye fatigue mitigation action is warranted is based on the determining that the blink rate of the user has slowed below the threshold value; track changes in a color of the sclera of an eye of the user; determine that the color of the sclera has changed indicating a state of fatigue of the eye of the user, where the determining that the eye fatigue mitigation action is warranted is based on the determining that the color of the sclera has changed; track a size of the pupil; determine the size of the pupil has increased without a corresponding ambient light decrease, based on the tracking the size of the pupil, where the determining that the eye fatigue mitigation action is warranted is based on the determining the size of the pupil has increased; estimate a distance from the camera to the pupil; calculate a distance from the pupil to the specified region based on the distance from the camera to the pupil; determine the pupil is too close to the specified region based on the distance from the pupil to the specified region being less than a predetermined value, where the determining that the eye fatigue mitigation action is warranted is based on the determining the pupil is too close to the specified region; track repetitive eye movements of the user based on the gaze direction of the user; and/or determine that a number of repetitive eye movements exceeds a predetermined value based on the tracking repetitive eye movements of the user, where the determining that the eye fatigue mitigation action is warranted is based on the determining the number of repetitive eye movements exceeds the predetermined value. In some embodiments, determining the gaze direction of the user includes determining a focus of the user by calculating a convergence of gaze direction from two eyes of the user, and convergence of gaze direction from two eyes of the user is calculated to be at the display; the determining the eye fatigue mitigation action is warranted is further based on determining a focus of the user is not at the display while both eyes each have a gaze direction toward the display; factors for determining that the eye fatigue mitigation action is warranted are controlled by an administrator account that controls actions of an electronic device of the display; the threshold value is based on criteria specific to the user; and/or determining the eye fatigue mitigation action is warranted is based on a plurality of criteria including blink rate and one or more of color of the sclera, blink velocity, or distance of the user from the specified region.

In some embodiments, a method for eye tracking includes receiving a plurality of visible light images acquired by a camera sensitive to visible light; tracking, using the plurality of visible light images a position of a pupil of a user in relation to the camera, where the plurality of visible light images are acquired over a time period; determining a gaze direction of the user over the time period, where gaze direction is based on the tracked position of the pupil; calculating a length of time during the time period that the gaze direction of the user is directed to a specified region; determining that the length of time the gaze direction of the user is directed to the specified region exceeds a threshold value within the time period; and/or determining, based on the length of time exceeding the threshold value, that an eye fatigue mitigation action is warranted to mitigate eye fatigue of the user. In some embodiments, the plurality of visible light images is a first plurality of visible light images; the time period is a first time period; the length of time is a first length of time; the threshold value is a first threshold value; and/or the method further comprises: receiving a second plurality of visible light images acquired by the camera, where the second plurality of visible light images are acquired over a second time period, and/or the second time period is after the first time period; calculating, using the second plurality of visible light images, that the gaze direction of the user is outside the specified region for a second length of time within the second time period; determining that the second length of time exceeds a second threshold value within the second time period; stopping the eye fatigue mitigation action based on determining that the second length of time exceeds the second threshold value; estimating a distance from the camera to the pupil; calculating a distance from the pupil to the specified region based on the distance from the camera to the pupil; determining the pupil is too close to the specified region based on the distance from the pupil to the specified region being less than a predetermined value, where the determining that the eye fatigue mitigation action is warranted is based on the determining the pupil is too close to the specified region; determining a first blink velocity of the user based on a first portion of the plurality of visible light images; determining a second blink velocity of the user based on a second portion of the plurality of visible light images; determining that blink velocity has slowed based on the second blink velocity being slower than the first blink velocity, where the determining that the eye fatigue mitigation action is warranted is based on the determining the blink velocity of the user has slowed; tracking a blink velocity of the user based on the plurality of visible light images; and/or determining the blink velocity has slowed below a threshold value based on the tracking the blink velocity of the user, where the determining that the eye fatigue mitigation action is warranted is based on the determining the blink velocity of the user has slowed below the threshold value. In some embodiments, the first threshold value can be adjusted after stopping the eye fatigue mitigation action to account for residual eye fatigue.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The detailed description is set forth with reference to the accompanying figures.

Figure 1:
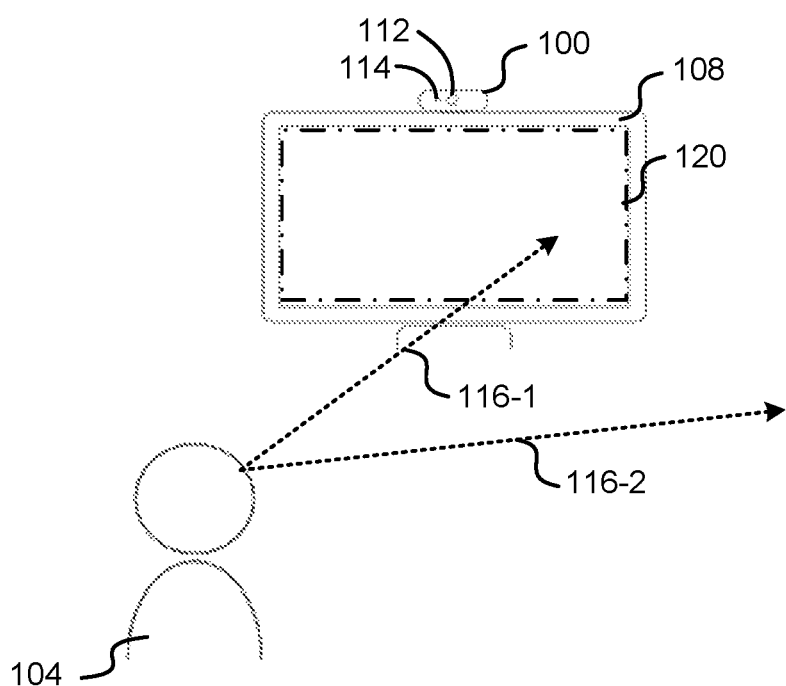
FIG. 1 shows a simplified diagram of an embodiment of a system for eye tracking to determine gaze direction of a user toward a monitor.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Embodiments of this invention are generally directed to electronic peripheral devices. More specifically, some embodiments relate to tracking eye movement and/or features to estimate eye fatigue of a user. Eye fatigue not only causes physical symptoms, it can also cause reduced productivity. After potential eye fatigue is determined, an eye fatigue mitigation action can be triggered. Eye fatigue mitigation action can including providing a notification, blurring a screen, or blanking a screen. Eye tracking can also be used to verify that a user diverted looking from a screen for a sufficient amount of time. By implementing eye fatigue mitigation actions, symptoms can be reduced and/or productivity increased.

In certain embodiments, a camera, configured to detect visible light, can be used to acquire a plurality of images. These images can be analyzed to track a location of a pupil of a user in relation to the camera over a time period (e.g., FIGS. 1-4). A gaze direction of the user can be determined based on the tracked location of the pupil. A length of time during the time period that the gaze direction of the user is directed to a specified region (e.g., a screen) may be calculated, which may account for very brief periods of time that the user may avert their eyes from the specified region (e.g., FIG. 5). In instances where the length of time the gaze direction of the user is directed to the specified region is determined to exceed a threshold value within the time period, an eye fatigue mitigation action may be triggered that can help the user recover from certain symptoms of eye strain. Other metrics may be used additionally or alternatively to help detect eye fatigue in a user including, but not limited to, a user's blink rate, changes in eye color, blink velocity, pupil size, and more (e.g., FIGS. 6-11), as further described in detail below.

A rule for mitigating eye strain can be called the 20-20-20 rule. The 20-20-20 rule states that to prevent eye fatigue while looking at monitor, a person it to look at something 20 feet away for 20 seconds after viewing a monitor for 20 minutes. However, many people don't follow the 20-20-20 rule. This disclosure relates to systems and methods for detecting potential eye fatigue, communicating to the user the potential eye fatigue, and/or verifying that eye fatigue mitigation actions have been implemented.

Referring first to FIG. 1, a simplified diagram of an embodiment of a system 100 for eye tracking to determine gaze direction of a user 104 toward a monitor 108 is shown. The system 100 comprises a camera 112 and optionally a light sensor 114 (e.g., used to detect ambient light). The camera comprises a lens and an image sensor. The image sensor can be configured to detect visible light. For example, the image sensor can be configured to detect red, blue, and/or green light to form an image.

The camera 112 can be configured to acquire a plurality of images of an eye of the user 104. The images can be visible light images (i.e., images that include image information in a visible light spectrum of wavelengths from about 380 to 740 nanometers). The system 100 comprises one or more processors configured to analyze the plurality of images. The system 100 can determine a gaze direction 116 of the user 104 based on analyzing the plurality of images. For example, pupil location in the plurality of images can be tracked. Pupil position relative to the camera can be based on a location of an image of the eye (e.g., image of the iris to determine pupil location) by an image sensor of the camera. Based on pupil location in the plurality of images, gaze direction 116 can be calculated. Features of a head of the user 104 can also be tracked. For example, a nose, a forehead, and/or an ear of the user 104 can be tracked to determine rotation of the head of the user 104. Rotation of the head of the user can also be used to determine gaze direction 116 of the user 104.

The system 100 can determine an X amount of time gaze direction 116 of the user 104 is directed to a specified region 120 in a Y window of time. The specified region is a display of an electronic device. In FIG. 1, the specified region 120 is a screen of the monitor 108. FIG. 1 shows a first gaze direction 116-1 and a second gaze direction 116-2. The first gaze direction 116-1 is directed toward the specified region 120. The second gaze direction 116-2 is directed to outside the specified region 120.

The system 100 can track, using the plurality of images detected by the camera 112 a location of the pupil of the user 104 in relation to the camera 112, wherein the plurality of images are acquired over a time period. For example, the time period is the Y window of time.

The system 100 can determine the gaze direction 116 of the user 104 of the time period, wherein gaze direction 116 can be based on the tracked location of the pupil.

The system 100 can calculate a length of time during the time period that the gaze direction 116 of the user 104 is directed to the specified region 120. For example, the length of time can be the X amount of time in the Y window of time. The system 100 can determine that the length of time that the gaze direction 116 of the user 104 is directed to the specified region 120 exceeds a threshold value within the time period. For example, the time period can be 30 minutes and the threshold value can be 25 minutes. In this example, if the user 104 looks at a screen longer than 25 minutes in a 30 minute window, then the threshold value can be exceeded. In some embodiments, the threshold value is a first threshold value and a second threshold value is used. The second threshold value can be a minimum amount of time that the gaze direction 116 is outside of the specified region. For example, the second threshold value can be 20 seconds; once the second threshold value has been met (i.e., the user 104 has a gaze direction 116 for more than 20 seconds outside the specified region 120), then the time period can be reset to zero.

Determining the gaze direction 116 can be binary, e.g., the gaze direction 116 can be determined to be directed toward the specified region 120 or not. For example, if the head of the user 104 is rotated away from the camera 112 and the pupil of the user 104 cannot be detected, the system 100 can determine that the user 104 is not looking at the specified region, even though the system cannot actively track the pupil of the user 104.

After the system 100 determines that the threshold value has been exceeded, the system 100 can trigger an eye fatigue mitigation action based on determining that the length of time that the gaze direction 116 of the user 104 is directed to the specified region 120 exceeds the threshold value.

Various options exist for an eye fatigue mitigation action. The eye fatigue mitigation action can include one or more of the following: blurring a screen, blanking a screen (e.g., with a solid color, such as black, or with a screen saver), providing a notification (e.g., a pop up or banner), reducing contrast, or transitioning the screen from color to back and white.

Applicant has found that in some embodiments, a gradual notification is preferable to an abrupt notification because doing so does not perturb the user 104 as much. For example, after thirty minutes of time have elapsed and having the screen go black could prevent the user 104 from sending an important email. Instead, the screen can be changed gradually. For example, the screen can start to become more blurry, colors could start to fade, and/or the screen could fade from a first state to a second state over time, wherein the first state is a normal display setting and the second state is a final state. In some embodiments, the final state can be blurry where the user 104 cannot read size 20 font, or the final state can be a black and white screen (which would allow the user 104 to continue to work). In some embodiments, the time it takes to transition from the first state to the second state is equal to or greater than 3, 5, 10, 30, 60, 120, 180, or 300 seconds and equal to or less than 0.2, 0.5, 1, 3, 5, 7, 10, 15, 20, 30, or 60 minutes.

Figure 2:
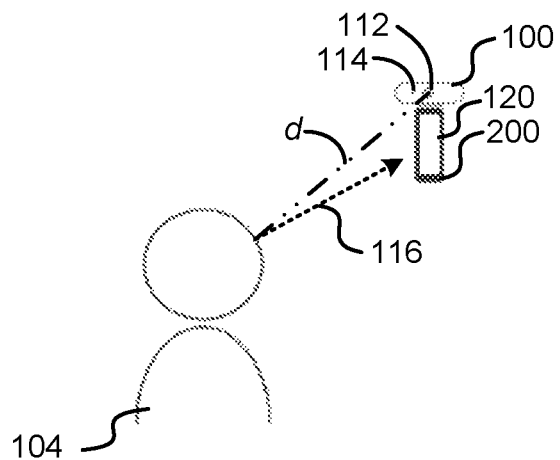
FIG. 2 shows a simplified diagram of an embodiment of a system for eye tracking to determine gaze direction of a user toward a mobile device.

FIG. 2 shows a simplified diagram of an embodiment of the system 100 for eye tracking to determine gaze direction of a user toward a mobile device 200. The specified region 120 in FIG. 2 is a screen of the mobile device. The gaze direction 116 of the user 104 is to the screen of the mobile device 200. Viewing distance from a screen can be about 1.5 times a width of the screen (e.g., measured diagonally). Viewing distance can also be a function of screen brightness.

They system 100 can determine, as disclosed herein, how far the user 104 is from the specified region 120 based on calculating a distance d from the camera 112 to the pupil of the user 104 and the relation of the camera 112 with the specified region 120. The system 100 can alert the user 104 if the user 104 is too close or too far from the screen of the mobile device. For example, the system 100 can trigger a distance-mitigation action. The distance mitigation action can be similar to the eye fatigue mitigation action or a different action. For example, eye-fatigue mitigation could cause the screen to blur, and the distance mitigation action could cause the screen to fade, with fade increasing in magnitude the closer the user 104 holds the mobile device to the pupil of the eye until turning dark when the distance from the device to the pupil is less than 0.6, 0.75, 0.8, 0.9, 1.0, or 1.1 times the width of the screen. In some embodiments, the distance-mitigation action is triggered when then distance from the eye to the specified region 120 is equal to or less than 1.4, 1.3, 1.2, or 1.0 times the width of the screen and/or equal to or greater than 1.7, 1.8, 1.9, 2.0, 2.2, or 2.5 times the width of the screen. Similarly to the eye fatigue mitigation action, the distance-mitigation action can change gradually.

In some embodiments, the distance-mitigation action is based on ambient light detected by the light sensor 114. If the screen is already dim, the distance-mitigation action could change contrast or change color rather than dimming the screen more. The eye fatigue mitigation action can be changed similarly. The distance-mitigation action can be helpful in teaching younger or newer users how far to be away from a screen.

In some embodiments, the camera 112, the light sensor 114, memory device, and/or processors are part of the mobile device 200, and when a mobile device app is loaded on the mobile device 200, then the mobile device 200 becomes the system 100.

Figure 3:
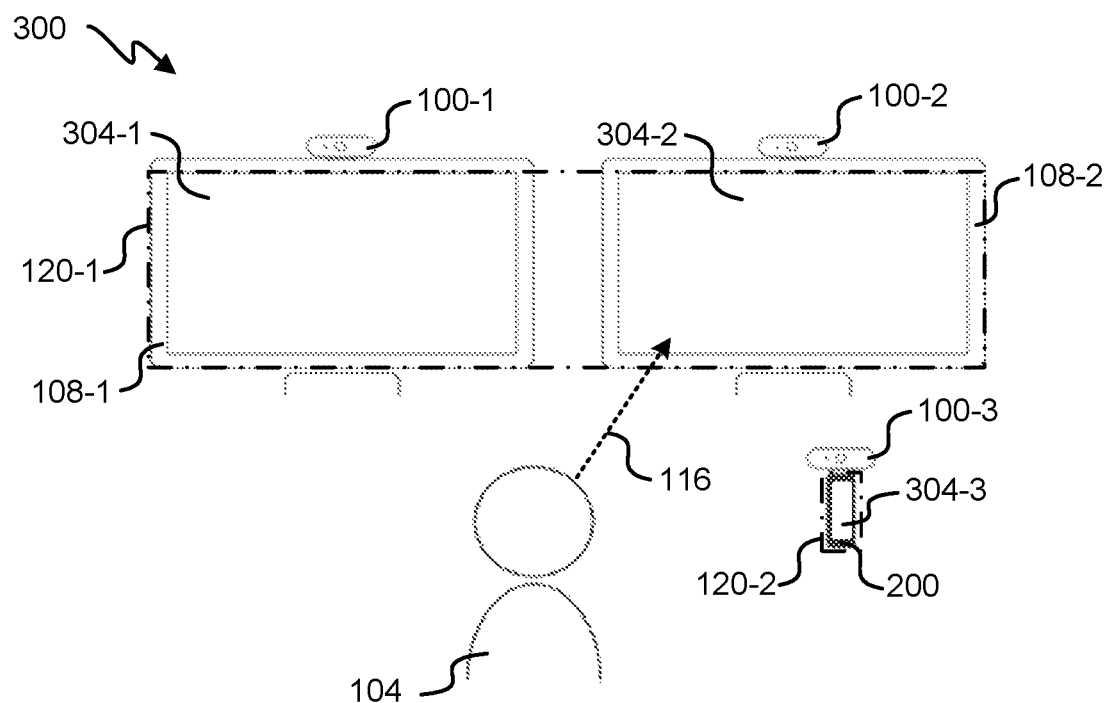
FIG. 3 shows a simplified diagram of an embodiment of a system for eye tracking to determine gaze direction of a user toward multiple displays.

FIG. 3 shows a simplified diagram of an embodiment of a combined system 300 for eye tracking to determine gaze direction 116 of a user 104 toward multiple displays. The combined system 300 comprises a first system 100-1, a second system 100-2, a third system 100-3, a first screen 304-1, a second screen 304-2, and a third screen 304-3. The first screen 304-1 is part of a first monitor 108-1. The second screen 304-2 is part of a second monitor 108-2. The third screen 304-3 is part of a mobile device 200. The first system 100-1 is attached to the first monitor 108-1. The second system 100-2 is attached to the second monitor 108-2. The third system 100-3 is attached to the mobile device 200. A first specified region 120-1 is a combination of the first screen 304-1, the second screen 304-2, and area between the first screen 304-1 and the second screen 304-2. The area between the first screen 304-1 and the second screen 304-2 can be part of the first specified region 120-1 because an eye of the user 104 usually does not change focus when changing gaze direction 116 from the first screen 304-1 to the second screen 304-2. A second specified region 120-2 includes the third screen 304-3. The combined system 300 does not include the user 104 or the gaze direction 116. In some embodiments, the combined system is the first system 100-1, the second system 100-2, and the third system 100-3.

The user 104 can have more than one display to look at. The combined system 300 tracks the gaze direction 116 of the user 104 to the specified region 120, which includes both the first specified region 120-1 and the second specified region 120-2. In some embodiments, the combined system 300 uses a software application (e.g., on a remote server, on a personal computer, on a mobile device, on a system 100) to coordinate eye tracking among multiple systems 100. Wired (e.g., Ethernet) and/or wireless connections (e.g., Wi-Fi, Bluetooth) are used to share data regarding gaze direction 116 of the user 104. The software application can retrieve display settings of devices to determine the specified region 120.

The user 104 can set up a user profile and/or an account. Eye tracking of the user 104 can be tailored to the user 104 (e.g., the system 100 and/or the combined system 300 can be trained per user 104). For example, different users may have different interpapillary distances, sizes of pupils, eye color, facial features, eyelid closure, etc. In some embodiments, an administration account is set up to monitor and/or control eye-fatigue mitigation and other controls.

Using the combined system 300, eye fatigue of the user 104 can be better monitored. For example, the user 104 could be viewing monitors 108 and then send a text using mobile device 200. The combined system 300 could track the time the user 104 views the monitors 108 and the time the user views the third screen 304-3 of the mobile device 200 to send the text as time toward triggering the eye fatigue mitigation action.

In some embodiments, dual thresholds of criteria for detecting eye fatigue are used. A first of the dual thresholds is a combination of criteria (e.g., length of time viewing a screen 304, color of the sclera of an eye, eyelid openness, blink rate, blink velocity, shape of pupil, etc.). The second of the dual thresholds can be when one criteria meets an extreme value (e.g., blink rate falls below four blinks per minute, or length of time viewing the screen 304 exceeds 30 minutes). Exceeding the second of the dual thresholds could trigger one mitigation action (e.g., screen goes fuzzy or blanks, preventing the user 104 from using a device) while exceeding the first of the dual thresholds triggers a second mitigation action (e.g., screen fades from color to black and white to allow the user 104 to continue to use the device).

The administrator account and/or the user account can be used to select mitigation actions and/or thresholds. After a mitigation action, a baseline of criteria can be adjusted to take into account that the eye may have residual fatigue. For example, a threshold could be lowered to take into account past days of high amounts of time viewing a screen 304. In another example, if the user did not look away from the screen for a long period of time, then the baseline could be increased so that the user can look at a screen for a less amount of time before a mitigation action is triggered.

Many variations are possible. For example, instead of using a camera of the third system 100-3 that is separate from the mobile device 200, the third system 100-3 could use a camera of the mobile device 200, as mentioned in the description of FIG. 2. The combined system could use the first system 100-1 for both the first monitor 108-1 and the second monitor 108-2 and not use the second system 100-2.

Figure 4:
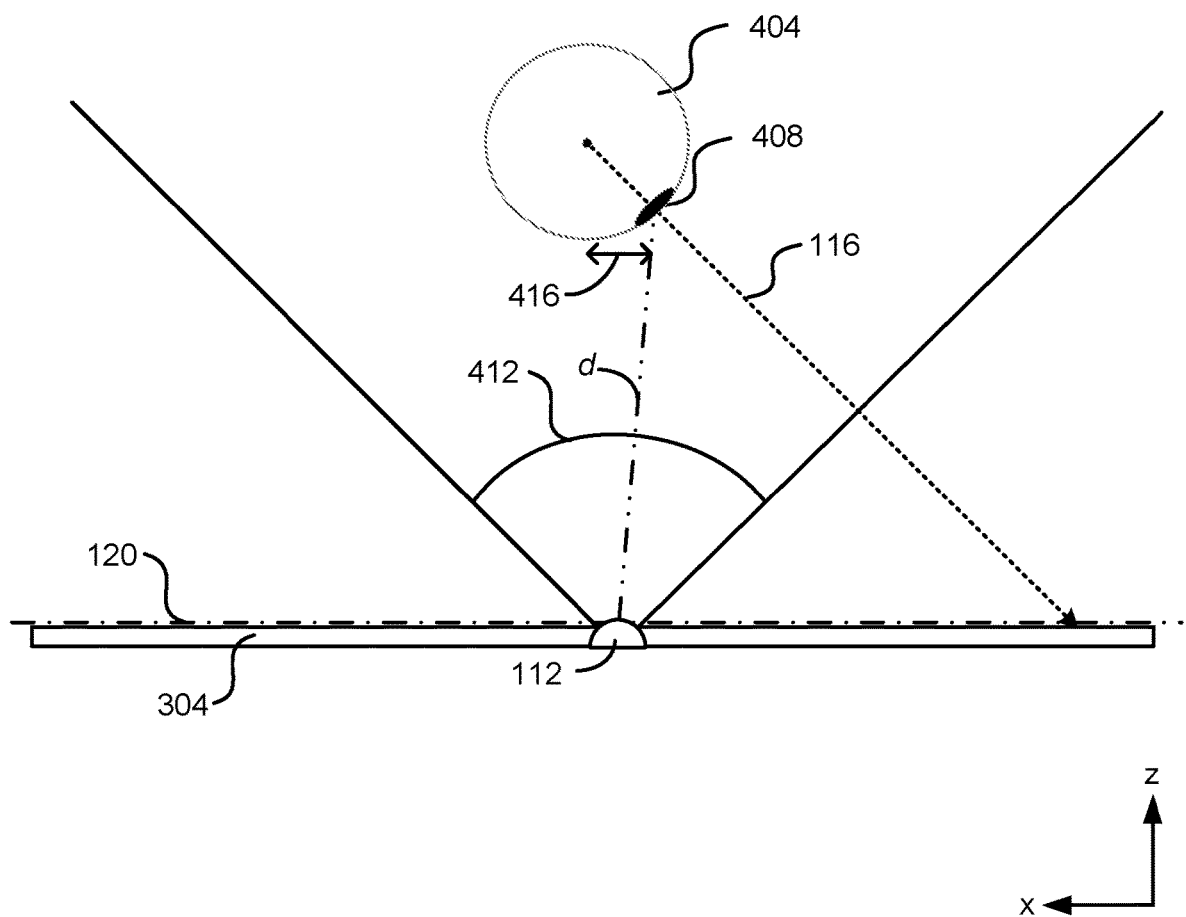
FIG. 4 is a simplified diagram of an embodiment for determining gaze direction to a specified region.

FIG. 4 is a simplified diagram of an embodiment for determining gaze direction 116 to a specified region 120. FIG. 4 shows an eyeball 404 of the user 104, a camera 112, and a screen 304. The eyeball 404 has a pupil 408 defined by an iris of the eye.

The camera 112 can comprise a lens and a sensor. The lens and the sensor can define a field of view 412 of the camera 112. The sensor can be sensitive to visible light. For example, the sensor can be a CMOS sensor having diodes sensitive to red, green, and blue light. The camera 112 can be used to identify and/or track features of the eyeball 404 and/or areas around the eye, such eyelids, eyebrows, nose, hair, etc.

A surface of the screen 304 can define an x-y plane, with a corresponding positive z dimension defined as being toward the user 104. The camera 112 can be placed to image the user 104 (e.g., an optical axis of the camera 112 can be pointed in the z direction). The sensor can be defined by a plane. The plane of the sensor is parallel to the plane of the screen 304 (e.g., +/−0, 3, 5, 10, or 20 degrees about the y axis and/or the x axis). The camera 112 can be positioned to be no farther than 2, 5, 10, 15, or 20 centimeters from the specified region 120. The specified region 120 can be an area in an x-y plane parallel on the x-y plane defined by the screen 304.

A distanced from the camera 112 to the pupil 408 can be calculated. For example, if a focal length of the lens of the camera 112 is known and a dimension of the user 104 is known (e.g., interpupilary distance of eyes of the user 104), then the distance d can be calculated (or estimated based on averages, such as the average interpupilary distance of a given population). In some embodiments, focal length of the eyes of the user is determined by detecting convergence of gaze direction of both eyes of the user. If convergence is closer to the user than the screen 304 is to the user, then focal length of the user is closer to the user than the screen 304. If convergence is farther from the user than the screen 304 is to the user, then focal length of the user is farther from the user than the screen 304. If convergence is at the screen 304, then the user is likely focusing on the screen 304. If the user is focusing closer or farther than the screen 304, then the user is likely not looking at the screen 304. Convergence can be used to detect whether a user is looking at the screen 304 for too long and/or to detect if the user has looked away. For example, convergence can be used to determine if the user is looking at an object more than 20 feet away from the user, such as to determine if the user is following the 20/20/20 rule. In some embodiments, non-convergence of gaze direction of both eyes, while gaze direction of both eyes is to the screen 304, can be an indicator of eye fatigue.

The system 100 can calculate the gaze direction 116 of the user. The system can calculate the gaze direction 116 by forming a vector from a center of the eye 404 through a center of the pupil 408. The center of the eye 404 can be determined by detecting a face and/or detecting landmarks on the face to identify a position of the eye 404. For example, a machine learning model, such as OpenFace, can be used to identify landmarks on the face and/or the eye 404. Landmarks on the face and/or eye can be used to determine a position of the center of the eye 404.

A center of the pupil can be determined by using infrared light. For example, infrared light can be directed to an eye, and the pupil will "glow" in an image acquired by an infrared camera. However, using a camera for pupil detection that is used to detected visible light (e.g., a camera in a smartphone or a camera used for video conferencing), under various lighting conditions, can be challenging. To use a camera that takes images of visible light, it can be observed that the center of the pupil is also the center of the iris. Eye regions can be extracted from images based on landmarks of the face. For example, in some machine learning models six landmarks can be identified around each eye, excluding the pupil. A portion of an image defined by a polygon having the six landmarks as vertices can be cut from an image. In some embodiments, two polygons, one for each eye, are cut from the image to form two extracted regions. Detecting an outline of an iris can be done using an extracted region.

An outline of the iris can be detected using machine learning or image processing. For example, image processing can include applying a dynamic threshold algorithm, morphological image processing, contour detection, ellipse fitting using RANSAC or Convex-Hull, and/or checking ellipse constraints. An outline of the iris can thus be found by detecting a gradient change (e.g., a threshold change in color, brightness, saturation, etc. over a threshold distance) indicative of a boundary between the sclera and the iris of the eye. An ellipse fit (e.g., using a best fit algorithm) to the outline of the iris estimates the outline of the iris. A center of the ellipse can be used to estimate the center of the iris, which would indicate the center of the pupil. A check can be made if an ellipse can be found in an extracted region of an image. If an ellipse cannot be found, another image can be used. A line can be drawn from the center of the eye through the center of the pupil to determine the gaze direction 116. Pupil displacement 416 can be calculated by the difference between the center of the eye 404 and the center of the pupil 408 in an image plane of a sensor of the camera 104.

In some embodiments, after determining a center of the pupil, a size of the pupil can be identified by analyzing an area of an image between the center of the pupil and the outline of the iris for a second gradient change. The second gradient change might be difficult to identify in the image as a whole, but by narrowing image analysis to an area within the iris, the second gradient change is more likely to be identified. A second ellipse can be fit to the second gradient change to determine a size (e.g., diameter) of the pupil.

In addition to the gaze direction 116, the system 100 can also track blink rate, blink velocity, color of the eye (e.g., redness of sclera), pupil dilation (e.g., without change in ambient light detected by light sensor 114), distance of the eye to the specified region 120, openness of eyelids, etc. In some embodiments, both eyes of the user 104 are tracked.

By tracking the pupil 408, other features (e.g., facial features such as eyelids), and/or motions, eye fatigue can be estimated. For example, if the pupil 408 increases in diameter without ambient light becoming dimmer, then that is a possible indication that the brain of user 104 is under strain;

or if a separation between a top eyelid and a bottom eyelid decreases, then that can possibly indicate drowsiness of the user 104. Repetitive eye movements can also indicate eye fatigue because the eye does not change direction as quickly while fatigued.

Figure 5:
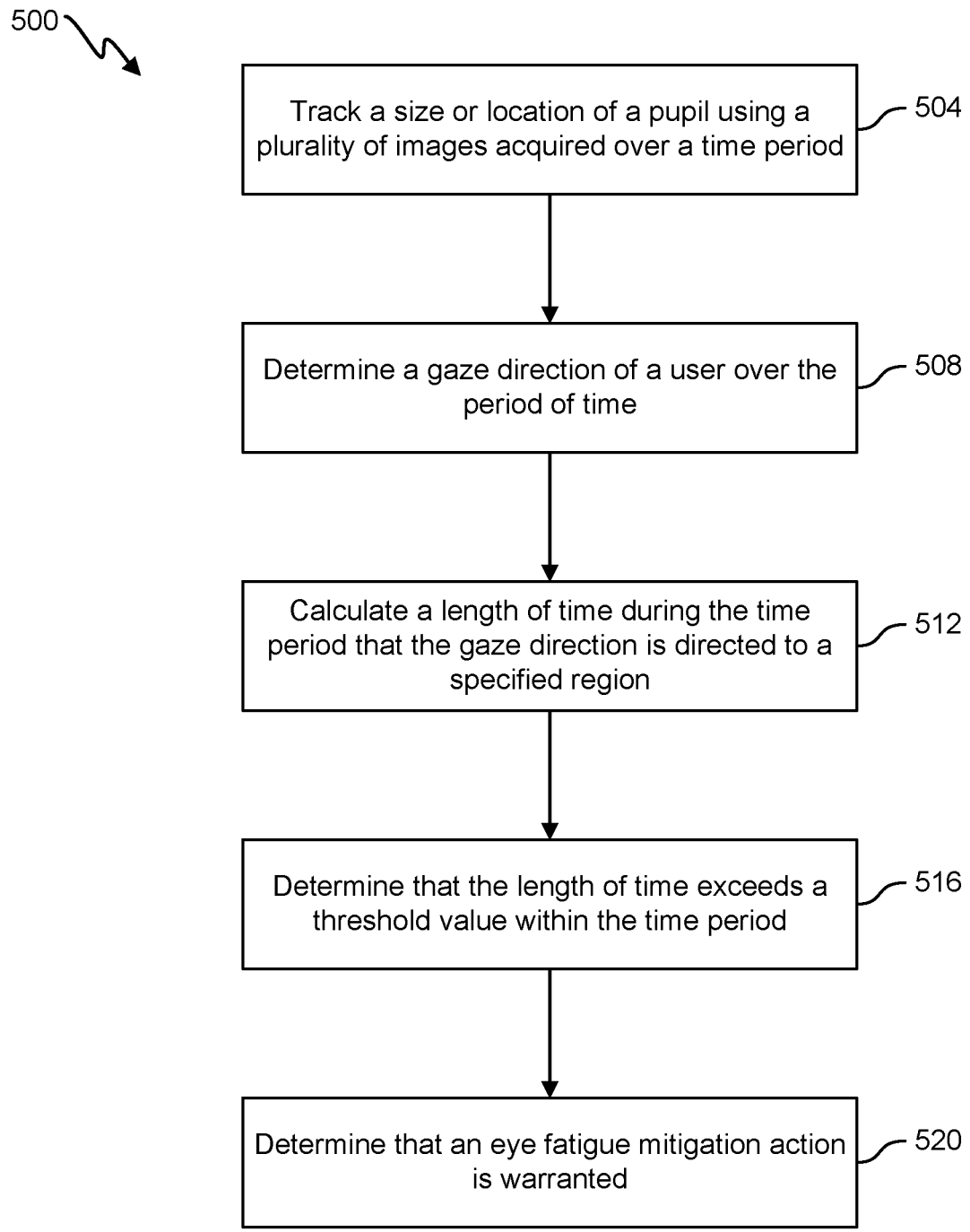
FIG. 5 illustrates a flowchart of an embodiment of a process for eye tracking to determine eye fatigue of a user.

FIG. 5 illustrates a flowchart of an embodiment of a process 500 for eye tracking to determine eye fatigue of a user 104. A plurality of images within the visible light spectrum can be acquired by a camera (e.g., camera 112 in system 100, a camera in a laptop computer, or a camera in a mobile device). Visible light cameras are readily available in laptop computer, mobile device, and as accessories. The plurality of images are acquired by the camera over a time period. In step 504, a location of a pupil (e.g., pupil 408) of a user (e.g., user 104) is tracked (e.g., in relation to the camera). The plurality of images are used for tracking the location of the pupil.

In step 508, a gaze direction (e.g., gaze direction 116) of the user is determined for the time period. The gaze direction is based on the tracked location of the pupil over the period of time. In some embodiments, a distance from the camera to the pupil (e.g., distance d) is calculated, and/or the gaze direction is based on the distance from the camera to the pupil.

In step 512 a length of time during the time period that the gaze direction of the user is directed to a specified region (e.g., the specified region 120) is calculated. The length of time can be how long the user is looking at a computer display within the time period.

In step 516, a determination is made that the length of time the gaze direction of the user is directed to the specified region exceeds a threshold value within the time period. The threshold could be a length of time or a percentage of time (e.g., length of time divided by the time period). In some embodiments the time period is a set time (e.g., 20, 25, 30, 40, 45, 60, 120 minutes; 1 day, 2 days, 1 week). In some embodiments, the time period is a rolling time period (e.g., resets after user looks outside the specified region for a set time (e.g., 20, 30, 40, 60, 120 seconds; 6 hours; 1 day).

In step 520, it can be determined that an eye fatigue mitigation action is warranted to mitigate eye fatigue of the user based on determining that the length of time the gaze direction of the user is directed to the specified region exceeds the threshold value. After determining that the eye fatigue mitigation action is warranted, the system 100 can trigger an eye fatigue mitigation action. The eye-fatigue mitigation can include blurring a screen (e.g., screen 304). The eye-mitigation action can be implemented gradually, such as gradually blurring, gradually fading, and/or gradually changing colors of the screen. The threshold value can be based on criteria specific to the user. For example, the threshold value can be changed based on how much the user has previously been viewing a screen or the threshold value can be set by an administrator specifically for the user.

In some embodiments, the threshold value is a first threshold value, the first threshold value is based on plurality of criteria, the eye fatigue mitigation action is configured to be triggered by a second threshold value, and/or the second threshold value is based on just one of the criteria exceeding an extreme threshold. For example, the first criteria includes a duration the gaze direction is toward the specified region and blink rate. Yet if blink rate slows more than four blinks a minute (e.g., an extreme threshold for blink rate), then the eye fatigue mitigation action could be triggered, regardless of the tracked direction the gaze direction is toward the specified region.

Repetitive eye movements of the user can also be tracked, based on the gaze direction of the user. It can be determined that a number of repetitive eye movements exceeds a predetermined value (e.g., saccadic eye movement is tracked). An eye fatigue mitigation action can be triggered based on determining that the number of repetitive eye movements exceeds the predetermined value. An eye fatigue mitigation action can be triggered if fixation does not change within a certain time.

Figure 6:
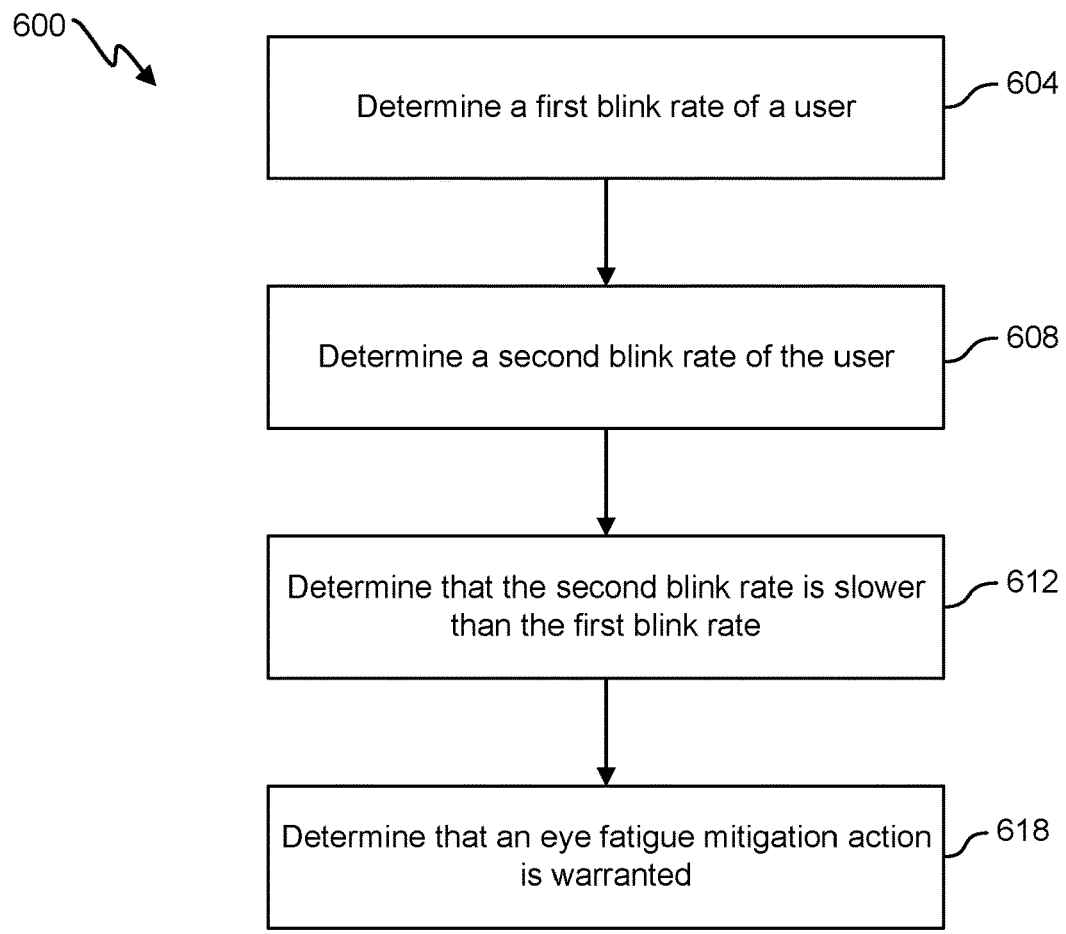
FIG. 6 illustrates a flowchart of an embodiment of a process for determining eye fatigue based on blink rate of the user.

FIG. 6 illustrates a flowchart of an embodiment of a process 600 for determining eye fatigue based on the blink rate of the user. Blinking gets slower as a person becomes more tired and can be an indicator of visual fatigue. Blink rate can be captured by a camera. Eyes at rest blink about 15 times per minute. Sustained visual tasks can reduce a blink rate to five blinks per minute. The user 104 can be notified to take a break if blink rate falls below 10, 8, 6, 5, and/or 4 blinks per minute. The user 104 could also be alerted to an anomalous blink rate. Blink completeness (opening eyelids completely after a blink) can also be monitored, as well as openness of eyelids (e.g., to detect drowsiness) and squinting.

Process 600 beings in step 604 with determining a first blink rate of the user for a first duration based on a first portion of the plurality of images. For example, the first duration can be one minute within a first fifteen minutes of the time period. The first portion of the plurality of images are images can be taken of the user during the first duration. The first portion of the plurality of images can be used to calculate the first blink rate. Image analysis can be used to determine how many times the user blinks during the first duration. In step 608, a second blink rate of the user for a second duration is determined. The second duration is after the first duration. The second blink rate is based on a second portion of the plurality of images. For example, the second duration can be a minute within a last fifteen minutes of the time period. The second portion of the plurality of images can be images taken of the user during the second duration. In some embodiments, the first duration and the second duration are in different time periods. The second blink rate can be compared to the first blink rate. In step 612, a determination can be made that the blink rate has slowed based on the second blink rate being slower than the first blink rate (e.g., by comparing the second blink rate to the first blink rate). In step 612, it can be determined that an eye fatigue mitigation action is warranted based on determining that the blink rate has slowed.

In some embodiments, a blink rate of the user is tracked based on a plurality of images, and a determination can be made that the blink rate has slowed below a threshold value (e.g., blinking is equal to or less than 10, 7, 5, or 3 times per minute). A determination can be made that the eye fatigue mitigation action is warranted based on determining that the blink rate of the user has slowed below the threshold value.

Figure 7:
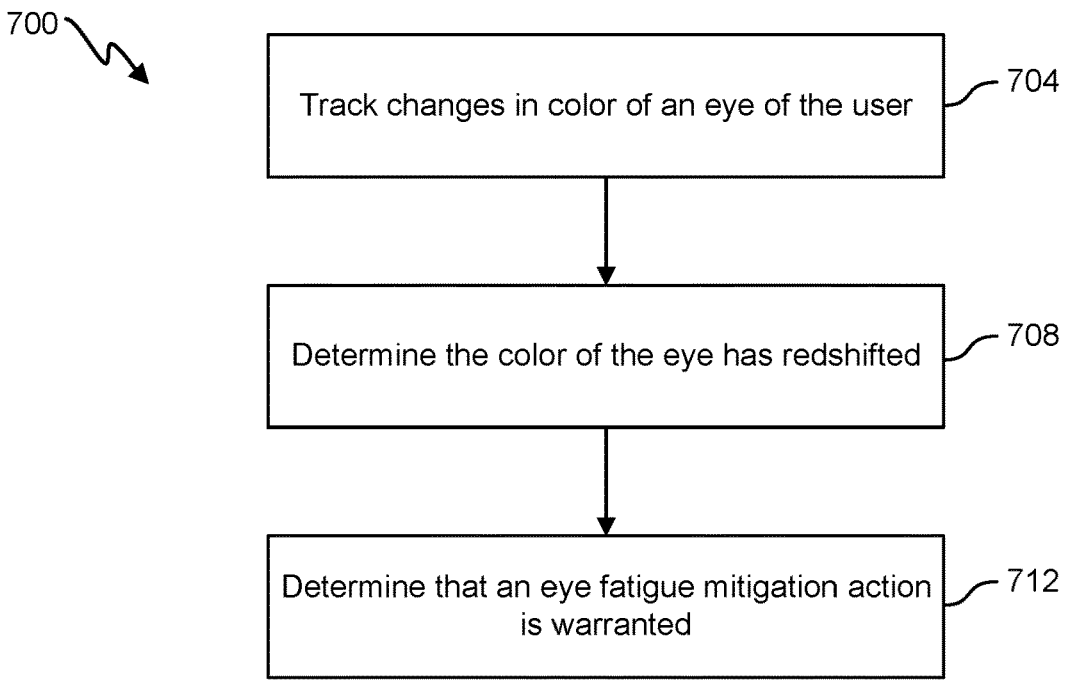
FIG. 7 illustrates a flowchart of an embodiment of a process for determining eye fatigue based on change in eye color of the user.

FIG. 7 illustrates a flowchart of an embodiment of a process 700 for determining eye fatigue based on change in eye color of the user. Color of the sclera, which is normally white, can change more reddish as tiredness of the user and eye fatigue increases. In process 700, a change in color of the eye (e.g., change in color of the sclera) is tracked, step 704. A determination is made that the color of the eye has redshifted (e.g., by wavelength analysis of light from the sclera averaged over an area of the sclera), step 708. In step 712, it can be determined that an eye fatigue mitigation action is warranted based on determining the color of the eye of the user has redshifted.

Figure 8:
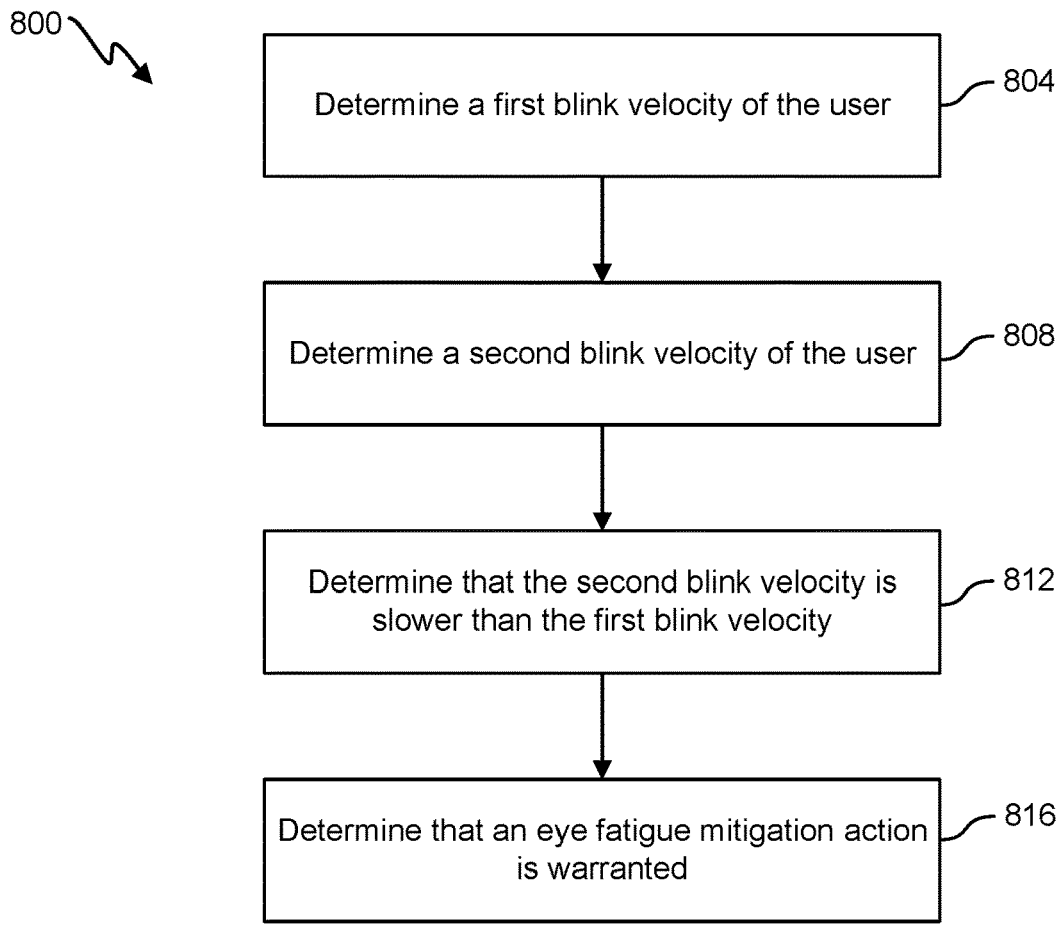
FIG. 8 illustrates a flowchart of an embodiment of a process for determining eye fatigue based on blink velocity of the user.

FIG. 8 illustrates a flowchart of an embodiment of a process 800 for determining eye fatigue. Blink velocity can slow as eye fatigue increases. Process 800 begins in step 804 with determining a first blink velocity of the user based on a first portion of the plurality of images (e.g., using images formed by detecting visible light). The first portion of the plurality of images can be images taken of the user during a first duration. The first portion of the plurality of images can be used to calculate the first blink velocity. Image analysis can be used to determine how fast the user blinks. A normal blink lasts about a tenth of a second. The camera 112 can have a frame rate equal to or greater than twenty frames per second (e.g., to meet or exceed a Nyquist criterion). Image analysis can include determining a first position and a second position of an eyelid (e.g., the first position is fully open and the second position is partially or fully closed). Images can be correlated to a clock, thus a change from the first position to the second position, and/or back to the first position, can be timed. A fully open position can be determined based on measurements of the eyelid in multiple images.

In step 808, a second blink velocity of the user can be determined based on a second portion of the plurality of images. The second portion of the plurality of images can be images taken of the user during a second duration. The second portion of the plurality of images can be used to calculate the second blink velocity. Image analysis can be used to determine how fast the second blink velocity is. In step 812, the second blink velocity is compared to the first blink velocity, and it can be determined that that blink velocity has slowed based on the second blink velocity being slower than the first blink velocity. In step 816, it can be determined that an eye fatigue mitigation action is warranted based on the determining that the blink velocity of the user has slowed.

In some embodiments, a blink velocity of the user can be tracked based on a plurality of images, and a determination can be made that the blink velocity has slowed below a threshold value (e.g., a blink takes longer than 0.25, 0.5, 1.0, 1.5, or 2.0 seconds). In some embodiments, a frame rate of a camera can be equal to or faster than a Nyquist criterion to detect a blink rate that has slowed below the threshold value (e.g., a frame rate equal to or greater than 8, 4, 2, 1.3, or 1 frames per second). A determination can be made that the eye fatigue mitigation action is warranted based on determining that the blink velocity of the user has slowed below the threshold value. In some embodiments, more than two blinks are used to determine eye fatigue. For example, a rolling average of blink velocity could be used to determine eye fatigue (e.g., tracking the average blink time of the last three, five, ten, or fifteen blinks). Excessively long blinks can be ignored. For example, a blink duration of more than five seconds can be ignored as someone intentionally closing their eyes. In some embodiments, if eyes are closed longer than a threshold value (e.g., 10, 15, 20, or 30 seconds), the screen can be darkened to save battery life of a device.

In some embodiments, a change of a fully open position (e.g., the fully open position is getting smaller) can also indicate eye fatigue of the user. A determination can be made that the eye fatigue mitigation action is warranted based determining that a fully open position of the eye is decreasing.

Figure 9:
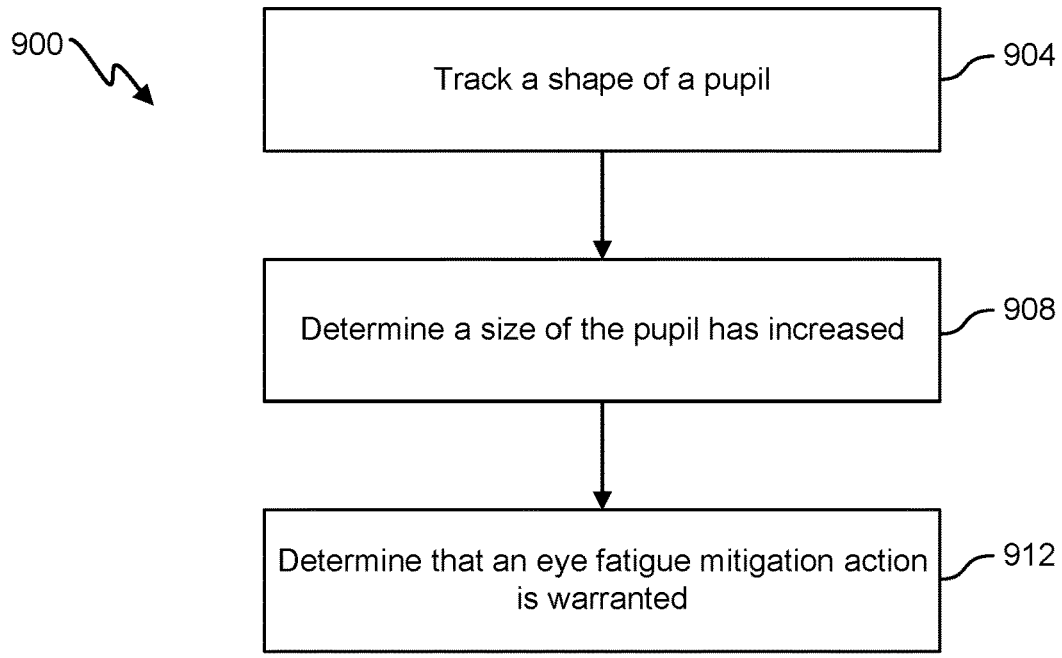
FIG. 9 illustrates a flowchart of an embodiment of a process for determining eye fatigue based on change in pupil size of the user.

FIG. 9 illustrates a flowchart of an embodiment of a process 900 for determining eye fatigue based on change in pupil size of the user. Increased pupil size, without a decrease in ambient light, is a possible indication the brain is under strain.

In process 900, the shape of the pupil is tracked, step 904. In step 908, a determination is made that the size of the pupil has increased without a corresponding ambient light decrease. In some embodiments, a size of the pupil is tracked. In step 912, it can be determined that an eye fatigue mitigation action is warranted based on determining the size of the pupil has increased.

Figure 10:
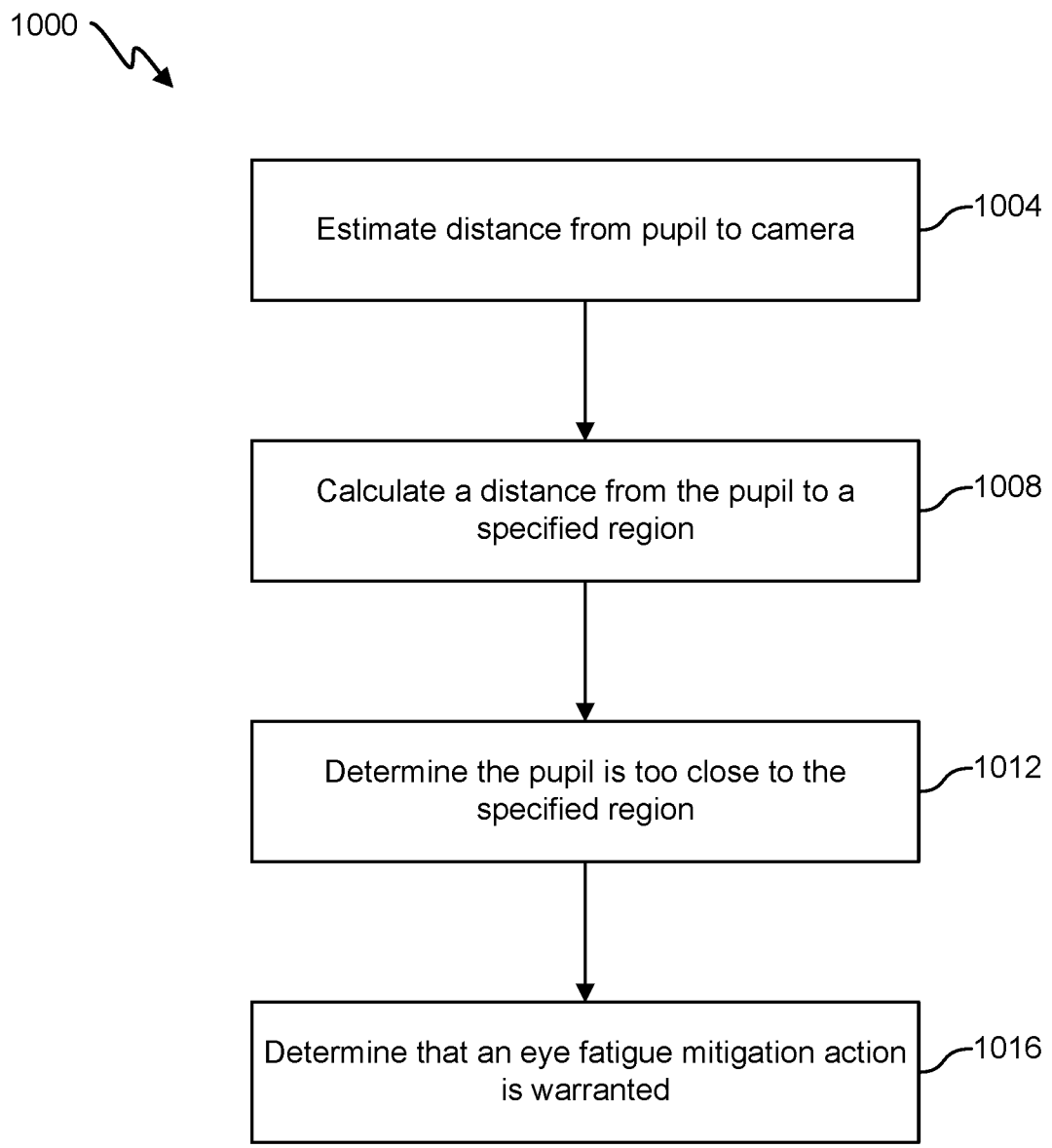
FIG. 10 illustrates a flowchart of an embodiment of a process for triggering eye-fatigue mitigation based on distance of a user from a display.

FIG. 10 illustrates a flowchart of an embodiment of a process 1000 for triggering eye-fatigue mitigation based on distance of a user from a display. A user positioned too close or too far from a screen 304 can cause eye strain. Process 1000 begins in step 1004 with estimating (e.g., calculating) a distance (e.g., distance d) from the pupil 408 to the camera 112. In step 1008, a distance from the pupil 408 to the specified region 120 is calculated.

A determination is made that the pupil 408 is too close to the specified region 120 based on the distance from the pupil 408 to the specified region 120 being less than a predetermined value, step 1012. For example, the specified region is a screen 304 and the predetermined value is based on a diagonal measurement of the screen (e.g., the predetermined value is 1.0, 1.1, 1.2, 1.3, 1.4, 1.5, or 1.6 times the diagonal measurement of the screen) and/or brightness of the screen (e.g., if the screen is bright, the predetermined value could be 1.6 times the diagonal measurement of the screen; if the screen is dim, the predetermined value could be 1.1). In step 1016, it can be determined that an eye fatigue mitigation action is warranted based on the determining the pupil 408 is too close to the specified region 120.

After it is determined that an eye fatigue mitigation action is warranted, an eye fatigue mitigation action can be triggered. For example, the screen 304 could be blurred, a display dimmed, and/or a notification is displayed instructing the user to back away from the screen 304.

Figure 11:
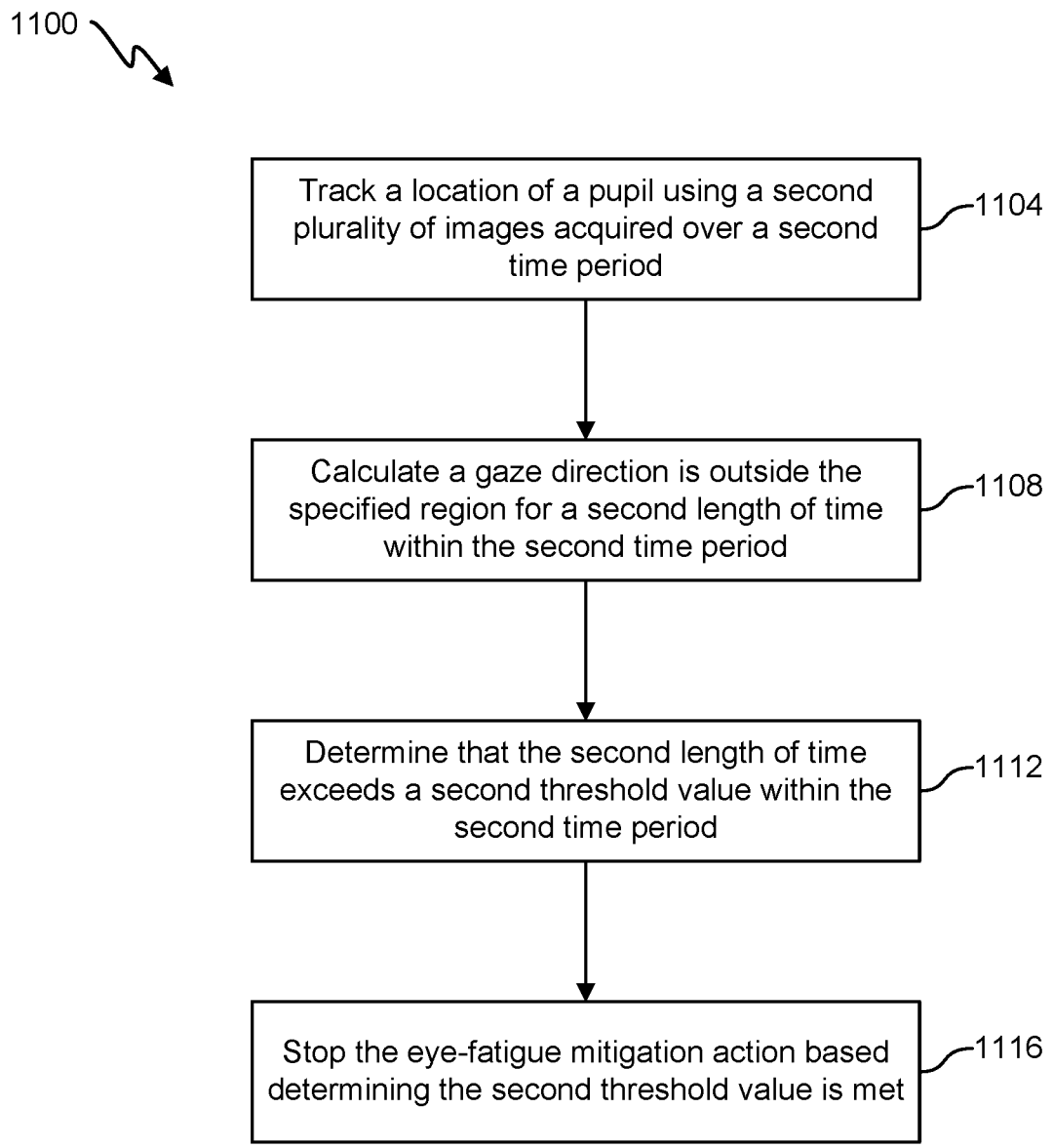
FIG. 11 illustrates a flowchart of an embodiment of a process for eye tracking to determine a user's eyes have rested.

FIG. 11 illustrates a flowchart of an embodiment of a process 1100 for eye tracking to determine a user's eyes have rested. Tracking eye(s) can be used to verify the user has looked away from a display. If the user has not looked away, the system 100 can prevent the user from using a screen 304 until the user has less eye fatigue.

In some embodiments, the plurality of images is a first plurality of images, the time period is a first time period, the length of time is a first length of time, and/or the threshold value is a first threshold value. Process 1100 begins in step 1104 with receiving a second plurality of images acquired by the camera, wherein: the second plurality of images are acquired over a second time period, and the second time period is after the first time period. For example, step 1104 occurs after an eye fatigue mitigation action is triggered (e.g., after step 520, 612, 712, 812, 912, and/or 1016).

In step 1108, the system 100 calculates, using the second plurality of images, that the gaze direction of the user is outside the specified region for a second length of time within the second time period. In step 1112, it is determined that the second length of time exceeds a second threshold value within the second time period. For example, the second length of time is 20 seconds and the second time period is 20 seconds; thus the user 104 has looked outside of the specified region 120 for 20 seconds.

In step 1116, the eye fatigue mitigation action is stopped based on determining that the second length of time exceeds the second threshold. In some embodiments, the first threshold is adjusted after stopping the eye fatigue mitigation action to account for residual eye fatigue.

Figure 12:
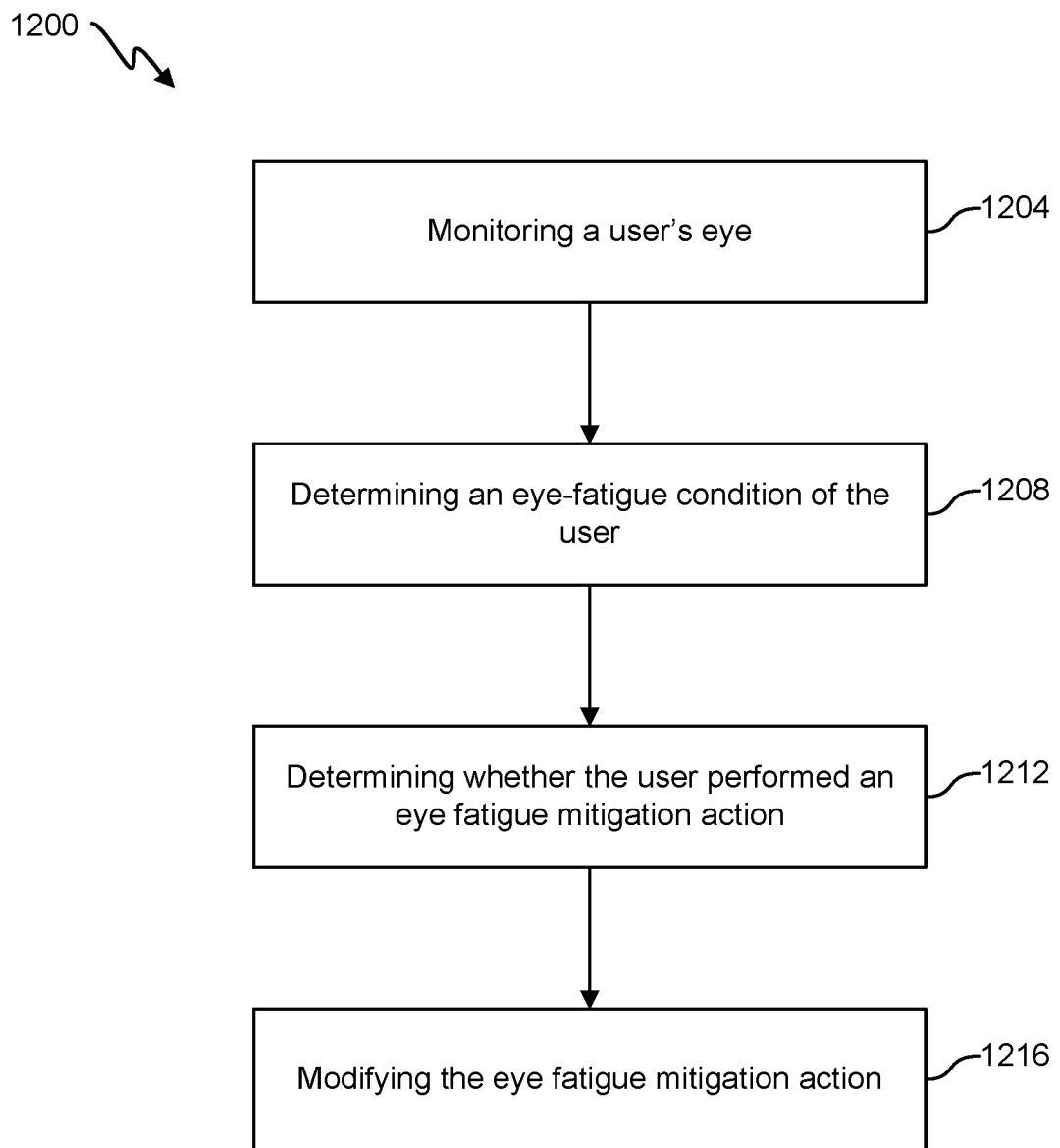
FIG. 12 illustrates a flowchart of an embodiment of a process for mitigating eye fatigue of a user.

Tracking that a gaze direction of a user is not toward a specified region is one way to verify eye-fatigue mitigation. There are other ways an eye fatigue mitigation action can be verified. FIG. 12 illustrates a flowchart of an embodiment of a process 1200 for mitigating eye fatigue of a user. Process 1200 begins in step 1204 with monitoring a user's eye. For example, a plurality of images detected by an image sensor of camera 112 of the system 100 is used to track a size and/or location of the user's eye. In step 1208, a determination is made that an eye-fatigue condition of the user exists based on the plurality of images. The user is requested to perform an eye fatigue mitigation action based on the determination that the eye-fatigue condition of the user exists. In step 1212, a determination is made whether the user is performing the eye fatigue mitigation action (EFMA). The camera 112 continues to acquire images after the request is made for the user to perform the eye fatigue mitigation action. In some embodiments, the plurality of images includes images acquired after the request for the user to perform the EFMA. The determination whether the user has performed the EFMA is based on the plurality of images. In step 1216, the request for the user to perform the EFMA is modified based on the determination whether the user has performed the EFMA.

For example, after step 1208, the user is sent a request in step 1212 that includes (A) a message (e.g., a pop-up, a push-notification to a mobile device) that the user's eyes are likely fatigued; and/or (B) an instruction to perform a mitigation action. An instruction to perform a mitigation action can include an instruction to look away from the display for a certain amount of time, perform certain eye exercises (e.g., blinking, tracking a dot, etc.). An EFMA can be tailored depending on a specific eye fatigue detected. For example, if blink rate has slowed, the user is instructed to blink n number of times in m seconds (e.g., blink five times in ten second). In some embodiments, a mitigation instruction is changed in real time if the user is not performing an aspect of the requested EFMA (e.g., a user is not focusing on an object far away).

Figure 13:
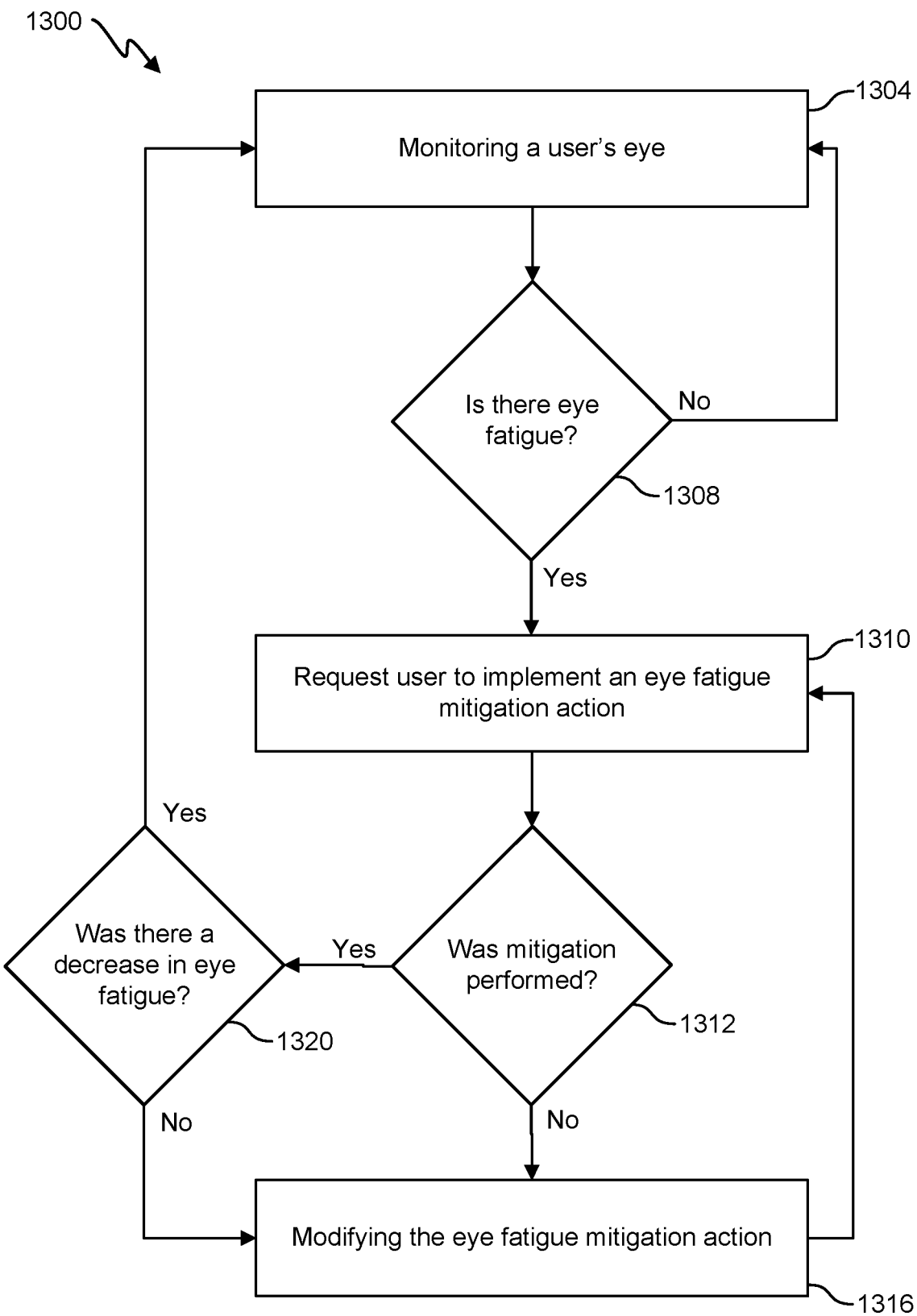
FIG. 13 illustrates a flowchart of an embodiment of a process for adjusting eye-fatigue mitigation.

FIG. 13 illustrates a flowchart of an embodiment of a process 1300 for adjusting eye-fatigue mitigation. Process 1300 begins in step 1304 with monitoring a user's eye. Step 1304 can be similar to step 1204. In step 1308 a decision is made whether there is eye fatigue (e.g., based on a plurality of images of the eye). If the answer is no in step 1308, the process 1300 returns to monitoring a user's eye, step 1304. If the answer is yes in step 1308, the process 1300 continues to step 1310. In step 1310, a request is sent to a user to implement an eye fatigue mitigation action (EFMA). For example, the request contains a message that the user could be experiencing eye fatigue and an instruction for the user to take an action. From step 1310, process 1300 continues to step 1312 where a decision is made whether the EFMA is performed. For example, the eye of the user is monitored and a decision is made that the user did not look away from a display for a long enough time. If the answer is no, then the process 1300 continues to step 1316.

If the answer is yes, then the process 1300 continues to step 1320.

In step 1316, the EFMA action can be modified, and process 1300 proceeds to step 1310 with a new EFMA requested for the user to perform. In step 1320, a decision is made whether there was a decrease in eye fatigue. If the answer is yes in step 1320, process 1300 returns to step 1304 with monitoring the user's eye. If the answer is no in step 1320, the process 1300 continues to step 1316 with modifying the EFMA.

In some embodiments, instead of the process 1300 returning to step 1316 after determining that eye fatigue has not been reduced in step 1320, an output of a display is adjusted to reduce user eye fatigue. For example, one, some, or all of the following of a display are adjusted to help reduce eye fatigue: color; sharpness; backlight settings; hue; tint; aspect ratio; font size; brightness; or contrast. In some embodiments, ambient lighting is detected using the plurality of images (e.g., video analytics), an ambient-light sensor (e.g., light sensor 114), and/or data from smart lighting fixtures in a room. Output of the display is based on the detected ambient lighting.

In step 1320, if eye fatigue has not been reduced, the user can be alerted to perform eye fatigue mitigation exercises based on the eye-fatigue condition of the user. The eye can be tracked to determine whether the user is performing the eye fatigue mitigation exercises. For example, the user can be alerted to blink a predetermined number of times within a time period, track a location of an icon on the display over the time period, and/or look away from the display at a location a predetermined distance past a location of the display relative to the user.

Requesting the user to look away from the display can include tracking a location and/or size of a user's pupil relative to the user's eye; and/or determining whether the user looked away from the display in response to the request based on the tracked location and/or size of the user's pupil. An alert can be generated for the user indicating that eye fatigue has not decreased, and the EFMA can be modified based on a most-recent detected eye fatigue condition of the user. If the user continues to not take action, the display can be turned off or turned black and white as discussed previously. An image sensor of a camera can be configured to detect light in only the visible spectrum.

Figure 14:
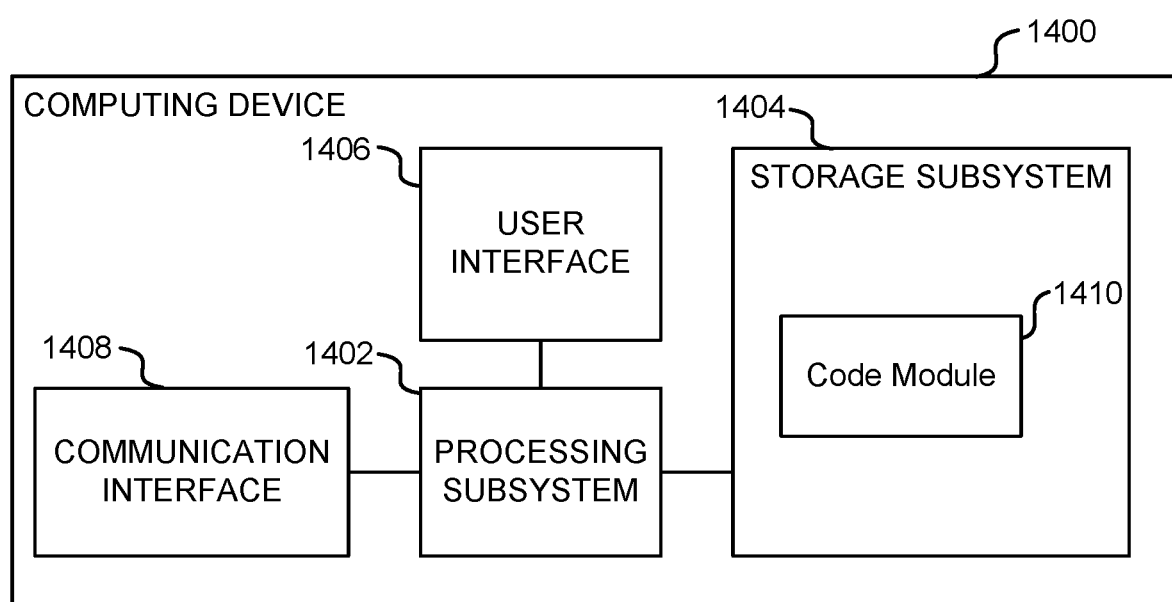
FIG. 14 depicts a block diagram of an embodiment of a computer system.

FIG. 14 is a simplified block diagram of a computing device 1400. Computing device 1400 can implement some or all functions, behaviors, and/or capabilities described above that would use electronic storage or processing, as well as other functions, behaviors, or capabilities not expressly described. Computing device 1400 includes a processing subsystem 1402, a storage subsystem 1404, a user interface 1406, and/or a communication interface 1408. Computing device 1400 can also include other components (not explicitly shown) such as a battery, power controllers, and other components operable to provide various enhanced capabilities. In various embodiments, computing device 1400 can be implemented in a desktop or laptop computer, mobile device (e.g., tablet computer, smart phone, mobile phone), wearable device, media device, application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or electronic units designed to perform a function or combination of functions described above.

Storage subsystem 1404 can be implemented using a local storage and/or removable storage medium, e.g., using disk, flash memory (e.g., secure digital card, universal serial bus flash drive), or any other non-transitory storage medium, or a combination of media, and can include volatile and/or non-volatile storage media. Local storage can include random access memory (RAM), including dynamic RAM (DRAM), static RAM (SRAM), or battery backed up RAM. In some embodiments, storage subsystem 1404 can store one or more applications and/or operating system programs to be executed by processing subsystem 1402, including programs to implement some or all operations described above that would be performed using a computer. For example, storage subsystem 1404 can store one or more code modules 1410 for implementing one or more method steps described above.

A firmware and/or software implementation may be implemented with modules (e.g., procedures, functions, and so on). A machine-readable medium tangibly embodying instructions may be used in implementing methodologies described herein. Code modules 1410 (e.g., instructions stored in memory) may be implemented within a processor or external to the processor. As used herein, the term "memory" refers to a type of long term, short term, volatile, nonvolatile, or other storage medium and is not to be limited to any particular type of memory or number of memories or type of media upon which memory is stored.

Moreover, the term "storage medium" or "storage device" may represent one or more memories for storing data, including read only memory (ROM), RAM, magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing instruction(s) and/or data.

Furthermore, embodiments may be implemented by hardware, software, scripting languages, firmware, middleware, microcode, hardware description languages, and/or any combination thereof. When implemented in software, firmware, middleware, scripting language, and/or microcode, program code or code segments to perform tasks may be stored in a machine readable medium such as a storage medium. A code segment (e.g., code module 1410) or machine-executable instruction may represent a procedure, a function, a subprogram, a program, a routine, a subroutine, a module, a software package, a script, a class, or a combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted by suitable means including memory sharing, message passing, token passing, network transmission, etc.

Implementation of the techniques, blocks, steps and means described above may be done in various ways. For example, these techniques, blocks, steps and means may be implemented in hardware, software, or a combination thereof. For a hardware implementation, the processing units may be implemented within one or more ASICs, DSPs, DSPDs, PLDs, FPGAs, processors, controllers, micro-controllers, microprocessors, other electronic units designed to perform the functions described above, and/or a combination thereof.

Each code module 1410 may comprise sets of instructions (codes) embodied on a computer-readable medium that directs a processor of a computing device 1400 to perform corresponding actions. The instructions may be configured to run in sequential order, in parallel (such as under different processing threads), or in a combination thereof. After loading a code module 1410 on a general purpose computer system, the general purpose computer is transformed into a special purpose computer system.

Computer programs incorporating various features described herein (e.g., in one or more code modules 1410) may be encoded and stored on various computer readable storage media. Computer readable media encoded with the program code may be packaged with a compatible electronic device, or the program code may be provided separately from electronic devices (e.g., via Internet download or as a separately packaged computer-readable storage medium). Storage subsystem 1404 can also store information useful for establishing network connections using the communication interface 1408.

User interface 1406 can include input devices (e.g., touch pad, touch screen, scroll wheel, click wheel, dial, button, switch, keypad, microphone, etc.), as well as output devices (e.g., video screen, indicator lights, speakers, headphone jacks, virtual- or augmented-reality display, etc.), together with supporting electronics (e.g., digital-to-analog or analog-to-digital converters, signal processors, etc.). A user can operate input devices of user interface 1406 to invoke the functionality of computing device 1400 and can view and/or hear output from computing device 1400 via output devices of user interface 1406. For some embodiments, the user interface 1406 might not be present (e.g., for a process using an ASIC).

Processing subsystem 1402 can be implemented as one or more processors (e.g., integrated circuits, one or more single-core or multi-core microprocessors, microcontrollers, central processing unit, graphics processing unit, etc.). In operation, processing subsystem 1402 can control the operation of computing device 1400. In some embodiments, processing subsystem 1402 can execute a variety of programs in response to program code and can maintain multiple concurrently executing programs or processes. At a given time, some or all of a program code to be executed can reside in processing subsystem 1402 and/or in storage media, such as storage subsystem 1404. Through programming, processing subsystem 1402 can provide various functionality for computing device 1400. Processing subsystem 1402 can also execute other programs to control other functions of computing device 1400, including programs that may be stored in storage subsystem 1404.

Communication interface 1408 can provide voice and/or data communication capability for computing device 1400. In some embodiments, communication interface 1408 can include radio frequency (RF) transceiver components for accessing wireless data networks (e.g., Wi-Fi network; 3G, 4G/LTE; etc.), mobile communication technologies, components for short-range wireless communication (e.g., using Bluetooth communication standards, NFC, etc.), other components, or combinations of technologies. In some embodiments, communication interface 1408 can provide wired connectivity (e.g., universal serial bus, Ethernet, universal asynchronous receiver/transmitter, etc.) in addition to, or in lieu of, a wireless interface. Communication interface 1408 can be implemented using a combination of hardware (e.g., driver circuits, antennas, modulators/demodulators, encoders/decoders, and other analog and/or digital signal processing circuits) and software components. In some embodiments, communication interface 1408 can support multiple communication channels concurrently. In some embodiments the communication interface 1408 is not used.

It will be appreciated that computing device 1400 is illustrative and that variations and modifications are possible. A computing device can have various functionality not specifically described (e.g., voice communication via cellular telephone networks) and can include components appropriate to such functionality.

Further, while the computing device 1400 is described with reference to particular blocks, it is to be understood that these blocks are defined for convenience of description and are not intended to imply a particular physical arrangement of component parts. For example, the processing subsystem 1402, the storage subsystem, the user interface 1406, and/or the communication interface 1408 can be in one device or distributed among multiple devices.

Further, the blocks need not correspond to physically distinct components. Blocks can be configured to perform various operations, e.g., by programming a processor or providing appropriate control circuitry, and various blocks might or might not be reconfigurable depending on how an initial configuration is obtained. Embodiments of the present invention can be realized in a variety of apparatus including electronic devices implemented using a combination of circuitry and software. Electronic devices described herein can be implemented using computing device 1400.

Various features described herein, e.g., methods, apparatus, computer-readable media and the like, can be realized using a combination of dedicated components, programmable processors, and/or other programmable devices. Processes described herein can be implemented on the same processor or different processors. Where components are described as being configured to perform certain operations, such configuration can be accomplished, e.g., by designing electronic circuits to perform the operation, by programming programmable electronic circuits (such as microprocessors) to perform the operation, or a combination thereof. Further, while the embodiments described above may make reference to specific hardware and software components, those skilled in the art will appreciate that different combinations of hardware and/or software components may also be used and that particular operations described as being implemented in hardware might be implemented in software or vice versa.

Specific details are given in the above description to provide an understanding of the embodiments. However, it is understood that the embodiments may be practiced without these specific details. In some instances, well-known circuits, processes, algorithms, structures, and techniques may be shown without unnecessary detail in order to avoid obscuring the embodiments.

While the principles of the disclosure have been described above in connection with specific apparatus and methods, it is to be understood that this description is made only by way of example and not as limitation on the scope of the disclosure. Embodiments were chosen and described in order to explain the principles of the invention and practical applications to enable others skilled in the art to utilize the invention in various embodiments and with various modifications, as are suited to a particular use contemplated. For example, the system 100 could be used to track posture, such as slouching or bending of the neck and trigger a mitigation action. It will be appreciated that the description is intended to cover modifications and equivalents.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc.

A recitation of "a", "an", or "the" is intended to mean "one or more" unless specifically indicated to the contrary. Patents, patent applications, publications, and descriptions mentioned here are incorporated by reference in their entirety for all purposes. None is admitted to be prior art.

What is claimed is:

1. A system for determining eye fatigue, the system comprising:
   a computing device having a screen;
   a camera comprising an image sensor, wherein:
      the image sensor is configured to detect visible light;
      the camera is attached to, or is part of, the computing device;
   one or more processors; and
   one or more non-transitory memory devices containing instructions that, when executed by the one or more processors, configure the one or more processors to:
      track, using a plurality of visible light images detected by the camera, a position of a pupil of a user in relation to the camera, wherein the plurality of visible light images are acquired over a time period;
      determine a gaze direction of the user over the time period, wherein gaze direction is based on the tracked position of the pupil;
      calculate a length of time during the time period that the gaze direction of the user is directed to a specified region corresponding to the screen of the computing device;
      determine that the length of time the gaze direction of the user is directed to the screen exceeds a threshold value within the time period considered to be unhealthy;
      determine, based on the length of time exceeding the threshold value, that an eye fatigue mitigation action is warranted to mitigate eye fatigue of the user; and
      trigger an eye fatigue mitigation action, based on determining that the eye fatigue mitigation action is warranted, wherein the eye fatigue mitigation action blurs the screen so that the user will be encouraged to look away from the screen.

2. The system of claim 1, wherein:
   the plurality of visible light images is a first plurality of visible light images;
   the time period is a first time period;
   the length of time is a first length of time;
   the threshold value is a first threshold value; and
   the instructions further configure the one or more processors to:
      receive a second plurality of visible light images acquired by the camera, wherein:
         the second plurality of visible light images are acquired over a second time period; and
         the second time period is after the first time period;
      calculate, using the second plurality of visible light images, that the gaze direction of the user not at the screen for a second length of time within the second time period;
      determine that the second length of time exceeds a second threshold value within the second time period; and
      stop the eye fatigue mitigation action based on determining that the second length of time exceeds the second threshold value, such that the user has looked away from the screen to mitigate eye fatigue, wherein stopping the eye fatigue mitigation action reverses blurring the screen.

3. An apparatus for determining eye fatigue, the apparatus comprising:
   a camera comprising an image sensor, wherein the image sensor is configured to detect visible light;

one or more processors; and
one or more non-transitory memory devices containing instructions that, when executed by the one or more processors, configure the one or more processors to:
  track, using a plurality of visible light images detected by the camera, a position of a pupil of a user in relation to the camera, wherein the plurality of visible light images are acquired over a time period;
  determine a gaze direction of the user over the time period, wherein gaze direction is based on the tracked position of the pupil;
  calculate a length of time during the time period that the gaze direction of the user is directed to a specified region corresponding to a display;
  determine that the length of time the gaze direction of the user is directed to the specified region exceeds a threshold value within the time period; and
  determine, based on the length of time exceeding the threshold value, that an eye fatigue mitigation action is warranted to mitigate eye fatigue of the user.

4. The apparatus of claim 3, wherein:
the instructions further configure the one or more processors to:
  determine a first blink rate of the user for a first duration based on a first portion of the plurality of visible light images;
  determine a second blink rate of the user for a second duration based on a second portion of the plurality of visible light images;
  determine that a blink rate of the user has slowed based on the second blink rate being slower than the first blink rate; and
the determining that the eye fatigue mitigation action is warranted is based on the determining that the blink rate of the user has slowed.

5. The apparatus of claim 3, wherein:
determining the gaze direction of the user includes determining a focus of the user by calculating a convergence of gaze direction from two eyes of the user, and
the convergence of gaze direction from two eyes of the user is calculated to be at the display.

6. The apparatus of claim 3, wherein the determining the eye fatigue mitigation action is warranted is further based on determining a focus of the user is not at the display while both eyes each have a gaze direction toward the display.

7. The apparatus of claim 3, wherein:
the threshold value is a first threshold value;
the instructions further configure the one or more processors to:
  track a blink rate of the user based on the plurality of visible light images; and
  determine that the blink rate has slowed below a second threshold value based on the tracking the blink rate of the user; and
the determining that the eye fatigue mitigation action is warranted is based on the determining that the blink rate of the user has slowed below the second threshold value.

8. The apparatus of claim 3, wherein:
the instructions further configure the one or more processors to:
  track changes in a color of the sclera of an eye of the user; and
  determine that the color of the sclera has changed indicating a state of fatigue of the eye of the user; and
the determining that the eye fatigue mitigation action is warranted is based on the determining that the color of the sclera has changed.

9. The apparatus of claim 3, wherein:
the instructions further configure the one or more processors to:
  track a size of the pupil; and
  determine the size of the pupil has increased without a corresponding ambient light decrease, based on the tracking the size of the pupil; and
the determining that the eye fatigue mitigation action is warranted is based on the determining the size of the pupil has increased.

10. The apparatus of claim 3, wherein:
the instructions further configure the one or more processors to:
  estimate a distance from the camera to the pupil;
  calculate a distance from the pupil to the specified region based on the distance from the camera to the pupil; and
  determine the pupil is too close to the specified region based on the distance from the pupil to the specified region being less than a predetermined value; and
the determining that the eye fatigue mitigation action is warranted is based on the determining the pupil is too close to the specified region.

11. The apparatus of claim 3, wherein factors for determining that the eye fatigue mitigation action is warranted are controlled by an administrator account that controls actions of an electronic device of the display.

12. The apparatus of claim 3, wherein:
the instructions further configure the one or more processors to:
  track repetitive eye movements of the user based on the gaze direction of the user; and
  determine that a number of repetitive eye movements exceeds a predetermined value based on the tracking repetitive eye movements of the user; and
the determining that the eye fatigue mitigation action is warranted is based on the determining the number of repetitive eye movements exceeds the predetermined value.

13. The apparatus of claim 3, wherein the threshold value is based on criteria specific to the user.

14. The apparatus of claim 3, wherein determining the eye fatigue mitigation action is warranted is based on a plurality of criteria including blink rate and one or more of color of the sclera, blink velocity, or distance of the user from the specified region.

15. A method for eye tracking, the method comprising:
receiving, using one or more processors, a plurality of visible light images acquired by a camera sensitive to visible light;
tracking, using the plurality of visible light images a position of a pupil of a user in relation to the camera, wherein the plurality of visible light images are acquired over a time period;
determining, using the one or more processors, a gaze direction of the user over the time period, wherein gaze direction is based on the tracked position of the pupil;
calculating, using the one or more processors, a length of time during the time period that the gaze direction of the user is directed to a specified region;
determining, using the one or more processors, that the length of time the gaze direction of the user is directed to the specified region exceeds a threshold value within the time period; and determining, using the one or more processors, that an eye fatigue mitigation action is warranted to mitigate eye fatigue of the user based on the length of time exceeding the threshold value.

16. The method of claim 15, wherein:

the plurality of visible light images is a first plurality of visible light images;

the time period is a first time period;

the length of time is a first length of time;

the threshold value is a first threshold value; and the method further comprises:

receiving a second plurality of visible light images acquired by the camera, wherein:

the second plurality of visible light images are acquired over a second time period; and the second time period is after the first time period;

calculating, using the second plurality of visible light images, that the gaze direction of the user is outside the specified region for a second length of time within the second time period;

determining that the second length of time exceeds a second threshold value within the second time period; and stopping the eye fatigue mitigation action based on determining that the second length of time exceeds the second threshold value.

17. The method of claim 16, wherein the first threshold value is adjusted after stopping the eye fatigue mitigation action to account for residual eye fatigue.

18. The method of claim 15, further comprising:

estimating a distance from the camera to the pupil;

calculating a distance from the pupil to the specified region based on the distance from the camera to the pupil; and determining the pupil is too close to the specified region based on the distance from the pupil to the specified region being less than a predetermined value, wherein the determining that the eye fatigue mitigation action is warranted is based on the determining the pupil is too close to the specified region.

19. The method of claim 15, further comprising:

determining a first blink velocity of the user based on a first portion of the plurality of visible light images;

determining a second blink velocity of the user based on a second portion of the plurality of visible light images; and determining that blink velocity has slowed based on the second blink velocity being slower than the first blink velocity, wherein the determining that the eye fatigue mitigation action is warranted is based on the determining the blink velocity of the user has slowed.

20. The method of claim 15, further comprising:

tracking a blink velocity of the user based on the plurality of visible light images; and determining the blink velocity has slowed below a threshold value based on the tracking the blink velocity of the user, wherein the determining that the eye fatigue mitigation action is warranted is based on the determining the blink velocity of the user has slowed below the threshold value.

\* \* \* \* \*